US011267850B2

(12) United States Patent
Spangenberg et al.

(10) Patent No.: US 11,267,850 B2
(45) Date of Patent: Mar. 8, 2022

(54) METABOLITE PRODUCTION IN ENDOPHYTES

(71) Applicant: Agriculture Victoria Services Pty Ltd, Attwood (AU)

(72) Inventors: German Carlos Spangenberg, Bundoora (AU); Kathryn Michaela Guthridge, Glenroy (AU); Ross Mann, Wendouree (AU); Timothy Ivor Sawbridge, Coburg (AU); Sophie Elizabeth Davidson, Heidelberg Heights (AU); Simone Vassiliadis, Essendon (AU); Inoka Kumari Hettiarachchige, Kingsbury (AU); Simone Jane Rochfort, Reservoir (AU); Emma Jane Isobel Ludlow, Viewbank (AU); Natasha Denise Brohier, Northcote (AU)

(73) Assignee: Agriculture Victoria Services PTY LTD, Bundoora (AU)

( * ) Notice: Subject to any disclaimer, the term of this patent is extended or adjusted under 35 U.S.C. 154(b) by 99 days.

(21) Appl. No.: 16/324,983

(22) PCT Filed: Aug. 11, 2017

(86) PCT No.: PCT/AU2017/050847
§ 371 (c)(1),
(2) Date: Feb. 12, 2019

(87) PCT Pub. No.: WO2018/027275
PCT Pub. Date: Feb. 15, 2018

(65) Prior Publication Data
US 2020/0270314 A1    Aug. 27, 2020

(30) Foreign Application Priority Data
Aug. 12, 2016  (AU) .................................. 2016903172

(51) Int. Cl.
C12N 15/82    (2006.01)
C07K 14/37    (2006.01)
A01H 17/00    (2006.01)
C12N 15/80    (2006.01)

(52) U.S. Cl.
CPC ............ C07K 14/37 (2013.01); A01H 17/00 (2013.01); C12N 15/80 (2013.01)

(58) Field of Classification Search
None
See application file for complete search history.

(56) References Cited

U.S. PATENT DOCUMENTS 8,884,100 B2 * 11/2014 Page .................. C12N 15/8243
800/278

OTHER PUBLICATIONS

Nicholson et al. (Molecular Cloning and Functional Analysis of Gene Clusters for the Biosynthesis of Indole-Diterpenes in Penicillium crustosum and P. janthinellum Toxins, 2015, vol. 7, pp. 2701-2722, doi:10.3390/toxins7082701.*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Doerks et al., (TIG, 14:248-250, 1998).*
Smith et al. (Nature Biotechnology, 15:1222-1223, 1997).*
Bork et al. (TIG, 12:425-427, 1996).*
McConnell et al. (Nature, 411:709-713, 2001).*
Hanzawa et al. (PNAS, 102:7748-7753, 2005).*
Wishart et al. (JBC, 270:26782-26785, 1995).*
Nishimura et al. (Plant Cell Physiol., 41 (5):583-590, 2000).*
Yang et al. (PNAS, 98:11438-11443, 2001).*
Young et al. (NCBI, GenBank Sequence Accession No. AY742903; Published Sep. 30, 2005).*
Young et al. (Mol Genet Genomics 274 (1), 13-29 (2005).*
Young et al. (NCBI, GenBank Sequence Accession No. DQ443465; Published Feb. 28, 2007).*
Young et al. (Fungal Genetics and Biology, 43:679-693, 2006).*
Hettiiarachighe et al. (BMC evolutionary Biology, 2015, vol. 15, e72, pp. 1-14).*
Penn, J. et al. "Janthitrems B and C, two principal indole-diterpenoids produced by Penicillium janthinellum" Phytochemistry, Jan. 1, 1993, pp. 1431-1434, vol. 32, No. 6.
Reddy, P. et al. "Thermogenic effects and functional metabolomics analysis of lolitrem B and its biosynthetic intermediates" Scientific Reports, Jun. 27, 2019, pp. 1-17, vol. 9, No. 1.
Anonymous—May 15, 2009 http://ibis.internal.epo.org/exam/dbfetch.jsp?id=EM_EST:G0845099; retrieved Dec. 4, 2019.
Babu, J. V., Bioactive Chemicals of Importance in Endophyte-Infected Grasses, PhD Thesis, University of Waikato, New Zealand.
Cogan, N. O.I et al., Development of a Transcriptome Atlas for Perennial Ryegrass (*Lolium perenne* L.), Abstracts 7th International Sumposium on Molecular Breeding of Forage and Turf, Jul. 2012, Salt Lake City, UT, USA, p. 86.
Gallagher, R. T. et al., The Janthitrems: Fluorescent Tremorgenic Toxins Produced by Penicillium janthinellum Isolates from Ryegrass Pastures; Applied and Environmental Microbiology, 1980, pp. 272-273, vol. 39, No. 1.
Guerre, P., Lolitrem B and Indole Diterpene Alkaloids Produce by Endophytic Fungi of the Genus *Epichloë* and Their Toxic Effects in Livestock, Toxins, 2016, pp. 1-16, vol. 8, e47, doi:10.3390/toxins8020047.

(Continued)

*Primary Examiner* — Vinod Kumar
(74) *Attorney, Agent, or Firm* — Larson & Anderson, LLC

(57) ABSTRACT

The present invention relates to nucleic acids encoding amino acid sequences for the biosynthesis of janthitrem in janthitrem producing endophytes. The present invention also relates to constructs and vectors including such nucleic acids, and related polypeptides, regulatory elements and methods.

5 Claims, 23 Drawing Sheets

Figure 4:
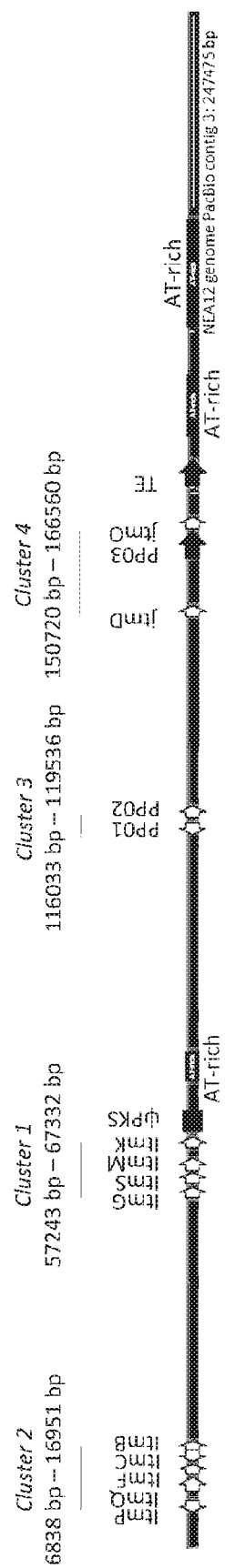

Specification includes a Sequence Listing.

(56) References Cited

OTHER PUBLICATIONS

Hennessy, L., Epoxy-janthitrems, effects of temperature on in planta expression and their bioactivity against porina larvae, MSc Thesis, 2015, University of Waikato, New Zealand.

Hettiarachchige, I. K. et al., Phylogenomics of asexual Epichloë fungal endophytes forming associations with perennial ryegrass; BMC Evolutionary Biology, 2015, pp. 1-14, vol. 15, e72, doi:10.1186/s12862-015-0349-6.

Liu, C. et al., Biosynthesis of Shearinine: Diversification of a Tandem Prenyl Moiety of Fungal Indole Diterpenes, Organic Letters, 2016, pp. 5026-5029, vol. 18, doi: 10.1021/acs.orglett.6b02482.

Nicholson, M. J. et al., Molecular Cloning and Functional Analysis of Gene Clusters for the Biosynthesis of Indole-Diterpenes in Penicillium crustosum and P. janthinellum, Toxins, 2015, pp. 2701-2722, vol. 7 (8).

Saikia, S. et al., The genetic basis for indole-diterpene chemical diversity in filamentous fungi, Mycological Research, 2008, pp. 184-199, vol. 112 (2).

Sawbridge, T. I., Genomic and Transcriptomic Analysis of Perennial Ryegrass/Epichloe Endophytes Symbiota, Abstracts Plant and Animal Genome XXIV Conference, Jan. 2016, p. 313, San Diego, CA, USA.

Stanke, M. et al., AUGUSTUS: a web server for gene prediction in eukaryotes that allows user-defined constraints, Nucleic Acids Research, 2005, pp. 465-467, vol. 33, doi: 10.1093/nar/gki458.

Young, C. A. et al., Molecular cloning and genetic analysis of a symbiosis-expressed gene cluster for lolitrem biosynthesis from a mutualistic endophyte of perennial ryegrass, Molecular Genetics and Genomics, 2005, pp. 13-29, vol. 274 (1).

Young, C. A. et al., A complex gene cluster for indole-diterpene biosynthesis in the grass endophyte Neotyphodium lolii, Fungal Genetic and Biology, 2006, pp. 679-693, vol. 43.

Young, C. A. et al., Indole-Diterpene Biosynthetic Capability of Epichloë Endophytes as Predicted by Itm Gene Analysis, Applied and Environmental Microbiology, 2009, pp. 2200-2211, vol. 75, No. 7, doi:10.1128/AEM.00953-08.

Pan et al.,—"Epichloe festucae isolate E2368 acetamidase and putative methyltransfe—Nucleotide—NCBI Accescion JF412802"—Aug. 17, 2011.

Hess et al.,—"CLS_CLiFpEfSpn_91a4_1_h18cLibkit5LD_D09CLS_CLiFpEfSPn_plant Festuca p—nucelotide—NCBI"—May 14, 2009.

Hess et al.,—"CLS_CLiFpEfSpn_91a4_1_h18cLibkit5LD_D09CLS_CLiFpEfSPn_plant Festuca p—nucelotide—NCBI GO883635"—May 14, 2009.

Hesse et al.,—"CLS_CLiFpEfSpn_121a8_1_I16cLibkit3LD_F08CLS_CLiFpEfSPn_plant Festuca—Nucelotide—NCBI GO845290"—May 14, 2009.

Hesse et al.,—"CLS_CLiFpEfSpn_121a4_1_I16cLibkit5LD_F08CLS_CLiFpEfSPn_plant Festuca—Nucelotide—NCBI GO845099"—May 14, 2009.

Hesse et al.,—"CLS_CLiFpEfSpn_91a4_1_h18cLibkit5LD_D09CLS_CLiFpEfSPn_plant Festuca—Nucelotide—NCBI EST :GO883635"—May 14, 2009.

Hesse al.,—"CLS_CLibFpEfS177_2p1_1_m05cLibkit5L_g03_CLS_cLibFpEfS177_plant Festuca—Nucelotide—NCBI GO790412"—May 14, 2009.

Hesse et al.,—"RDD_cLiFpEfl12nb_7x1_2_C10_cLibkit5_B05RDD_cLiFpEfl12nb_plant Festuca—Nucelotide—NCBI GO895983"—May 14, 2009.

Kohler et al.,—"Oidiodendron maius Zn unplaced genomic scaffold scaffold_18, whole gen—Nucleotide—NCBI—Too many links for CiteNpl:2512"—Jan. 10, 2015.

\* cited by examiner

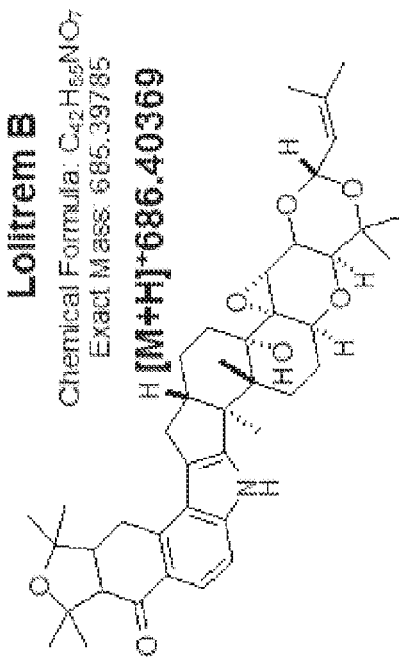
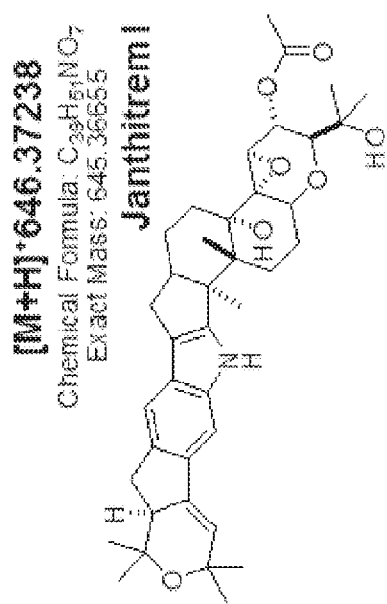
Figure 1

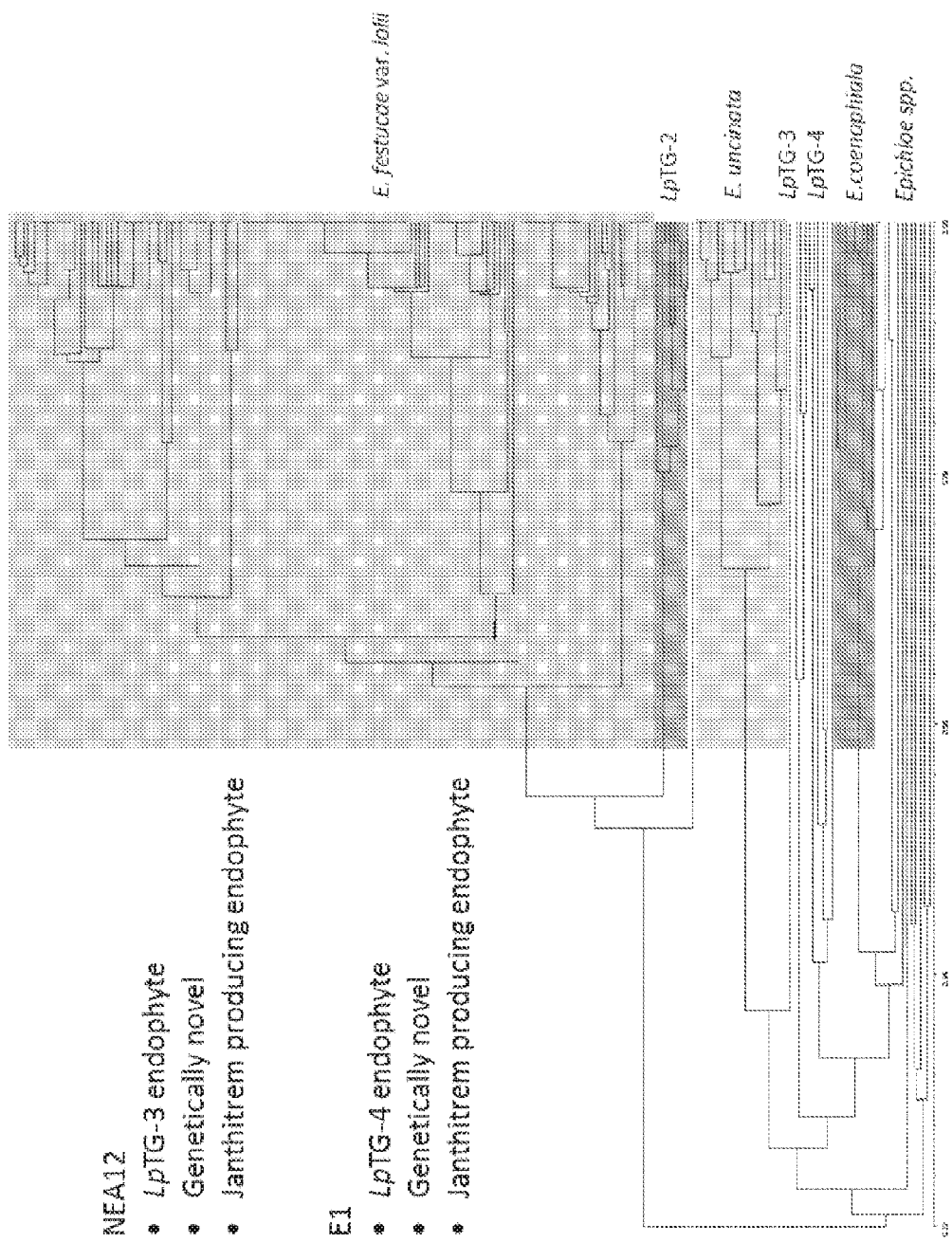

| Alkaloid | Gene | Endophyte species and strain | | | | | | | | | | | | | | | | | | |
|---|---|---|---|---|---|---|---|---|---|---|---|---|---|---|---|---|---|---|---|---|
| | | Epichloë festucae var. lolii | | | | | | | | | | | LpTG-2 | | | LpTG-3 | | | LpTG-4 |
| | | E9 | 15335 | AR1 | 15441 | SE | C9 | NA6 | 15714 | NEA10 | NEA2 | 15931 | 44F2 | NEA3 | 67A1 | NEA11 | NEA4 | NEA12 | 15310 | 15311 | E1 |
| Peramine | perA | + | + | + | + | + | + | + | + | + | + | + | + | + | + | + | + | / | / | / | / |
| Ergot Alkaloids | dmaW | | + | + | + | + | + | + | + | + | + | + | + | + | + | + | + | | | | + |
| | easA | | + | + | + | + | + | + | + | + | + | + | + | + | + | + | + | | | | + |
| | easE | | + | + | + | + | + | + | + | + | + | + | + | + | + | + | + | | | | + |
| | easF | | + | + | + | + | + | + | + | + | + | + | + | + | + | + | + | | | | + |
| | easG | + | + | + | + | + | + | + | + | + | + | + | + | + | + | + | + | | | | + |
| | easH | | + | + | + | + | + | + | + | + | + | + | + | + | + | + | + | | | | + |
| | lpsA | + | + | + | + | + | + | + | + | + | + | + | + | + | + | + | + | | | | + |
| | lpsB | + | + | + | + | + | + | + | + | + | + | + | + | + | + | + | + | | | | + |
| Lolitrems | ltmG | + | + | + | + | + | + | + | + | + | + | + | + | + | + | + | + | + | + | + | + |
| | ltmM | + | + | + | + | + | + | + | + | + | + | + | + | + | + | + | + | + | + | + | + |
| | ltmK | + | + | + | + | + | + | + | + | + | + | + | + | + | + | + | + | + | + | + | + |
| | ltmB | + | + | + | + | + | + | + | + | + | + | + | + | + | + | + | + | + | + | + | + |
| | ltmC | + | + | + | + | + | + | + | + | + | + | + | + | + | + | + | + | + | + | + | + |
| | ltmF | + | + | + | + | + | + | + | + | + | + | + | + | + | + | + | + | + | + | + | + |
| | ltmP | + | + | + | + | + | + | + | + | + | + | + | + | + | + | + | + | + | + | + | + |
| | ltmQ | + | + | + | + | + | + | + | + | + | + | + | + | + | + | + | + | + | + | + | + |
| | ltmE | | + | | + | + | + | + | + | + | + | + | + | + | + | | | | | | |
| | ltmJ | + | + | + | + | + | + | + | + | + | + | + | + | + | + | | | | | | |
| Expected phenotype | | LP | LP | EP | LEP | LEP | LEP | LEP | LEP | EP | EP | EP | EP | EP | LP | EP | EP | | | | E |
| Observed phenotype | | LP | LP | P | LEP | LEP | LEP | LEP | LEP | EP | EP | EP | EP | EP | N.D. | EP | EP | | | | |

Figure 3

>PP01

[atgccgtcatttccgagtctgcaatcggtcctcccaggcatggctcatcagtggctcagtgctgctgtcggacagatggtggcgtcg
cggccgtcgtcttgacgacggagccgctgctctgctctcgtgaccggcggcccgatttctcgactttcttcggcatgtcctggactttat
gggatcccaggcggcagtttagcttagcttcttcttatggaccgtactttctacgactgcgcggcgcctggactttat
cccaggjGTATATCTTCAATTTAATGCTCGTCAAAACGGGCCGTGGGCGAGCTGACACGCGTGAAATGCTAG|CTTTCTGGCCCTCGTTGCCGAGCGCCGAGCGCCGAGGATCG
AGCACCTCCTTGCCGACCCTCTCTTTCAAGCAATTCATGCTCAAGCGACAAGAGCACGCTCGCGTTACCTCGCAGCGCCTGACCCTACGG
AGACTGCCCTTTGGCGCCATGACACATCGTTGCCGGTTAAGGCTAGAGCTTCAGCTCACCGCCTCTCGGAGCAGGCACGACATTT
TCCGACGACCCCAAGCTGCTGCCGACACGTGTCTGGCAAGTTGGACTCCTCGACGATCGTTGGCTCTCCAAGACATCGGAGGCATGTTCCCTGCCCATGCAGACATGCATTGATGGATCA
GCAAGATGCTCGCCGGTGCCAAGTTGCACCGCGTGCTCCCAAAATTCACGAGCGAGCGCCCAAAGACCGCAGAACAAGAGGATGCAAGGATGTGCGTACATGTAG
AGGCCACCGGGATACGACATCGGTCTGCC]GTACGCCCTGGTCCCCCCGTCTCCCGCTCTTACCTCGAAGCCTTGCGACACTTATACCTCGACACTTATACCTCGACACTTATACCTCGAAG[CTCATCATCGGCGCC
CTCAGTCGAGGACTTGCCAATACGGCTTCAGTGCCGCGTTAACGTGCATCCTCGGCGCCTGGATCCTCGACAGACCCGGAGTTCCGAGTTCGCGACGCTGCTG
TTCCCAAGTACACCGCGGGTGGAGTCGGCGGGCCGGAAGTTCCTCTTGGCCCCGAAGTTCCCAAGGGAGGTGGGAGTTCCAATGATTCGCACGGCCGATCGGA
GACGATCCATCGATCGATCGCAGTCAGTCAAACGTAAAAATATTAGCGCGCATAATTCGGAAACGGCATCATCGCCACTTT]GTACTTCGTACAAAA
TAAATTAAATATAAATATGTGAACTAATTCAATAAATTCTTTATTGATCGGACTATATCTTGATCTTTTAACTTAACTATTTTAAGAATTGGGggaaggaaagtt
agctacttagtctttcttcttcttcttcttcttcttcttcttcttcttaatactatattaacacccttattataqcttactag]

Figure 7

```
PPO1          1  MPSIPSLASGLQAWLISGVVLLAAAVLVGQMAASRPRLDDRAPRLLKG      50
                   |:.|:.:||:::|||::|||.|:|:||.....::||||||
Hm(KJZ77225)  1  -----SLIPGEAWPASVLMLLTGAAAIVIQMVASRPSFPSGAPRLLKG      45

PPO1         51  APILGCLDFFRCRSEFLLKGRDRDPSRQFSFFYGPYPTVALSGSAARSFF    100
                  ||||||||| |||||||||||:|||||||||||.|::||:|||||||||
Hm(KJZ77225) 46  TPILGCLDFFRSRSEFLLKGRDNDPSRQFSFYYGPEPIVVSGSSARSFF      95

PPO1        101  YTARGLDFIPGFLALVAAGPSIEQLLPGGDFRTLFVSSFKEFMHKKQLAA    150
                  |:|||||:|.|||:|||||:|:...||..|.|:|.:|||:||:|:.:.|
Hm(KJZ77225) 96  YNARGLDLQAGFSTLFAAGPSLDH-LHTGDIRTIFITSEKELMHKDRLQA    144

PPO1        151  NLGYLTTDADVALGAIDTSLPVEPFKLMLHLIYQLSHRVLGREDISDDPK    200
                  |:|.:|.||||||.||..::|..|:::|||||||||.:||.:|:|:.||
Hm(KJZ77225)145  NLHHLVNDADVALGGLDVSRPVEPFRVMLHLIYQLTHRTLGSNDIAENPK    194

PPO1        201  LLADTVSAFGLLDDSSALEVMFPRVFWPSKVRKMLAGAKLFRVLSKITSD    250
                  |||.|:|:||||:|||:||:|.|||.|||||:|::||||:.|.:.:.:|
Hm(KJZ77225)195  LIAKTLESFGRLDDSSAMEIMFPWVFWPSKMKKMVAGAKLFRTFSNIMND    244

PPO1        251  RRKTRRTKRDAMQTLMDQGEPDTIVSALIIGALSAGLANSAFSAAWILAY    300
                  ||:|.|.:|||||||||||:|.|||||::||||:||..|||||||||||
Hm(KJZ77225)245  RRRTGRVEPDAMQTLMDQGHQDLIISIFIIGALFAGLINSAFSAAWILAY    294

PPO1        301  LSVNREWYARIRAEVDAAVAKHRRSRVESAPEVLLRLSMGEWESEFPMIC    350
                  |:.||||||||:.|||||||||:||:|||||:||:||||..|.||.::.
Hm(KJZ77225)295  LTNNPEWYARIRNEIDAAVAKHRYSEQESAPKVLARLSMDDWETEFPMVD    344

PPO1        351  TALRETIRVMLQLTSIRKNISGKDIQIAETGIIALST                387
                   |||||||||:|.:|:.|
Hm(KJZ77225)345  LALRETIRVLQGSSMRKNVSGQDIPIGDTGQI-----                377

Figure 8
```

>PP02
cgagcatcaagccgcgtgccgaggaatgtcggacattggccgaggcgtacatgacgtatacatcaagccgcaccactgactgcagcctagaacagatggcata
gttggatatgttgcttcgttattacgtaccgcgccaataatctcctcttgcttcatatctcttgcattaatcccgaaccccttcgtgactgtgctctgtggcggaacacagattccggttgccta
aagcccatcaaggccgatccggttctgtcttcatatctcttgcattaatcccgaaccccttcgtgactgtgctctgtggcggaacacagattccggttgccta
ctcagcggcaacagttggtaccccgtggtgacgatccttggagcttgctgccggataatcatgccgaccggttcttgcctccaatgttccccatcttgatgact
atttctcttacctcggatactacactcgtcggccattcgccttgtctattgcggcataatattatgccgtcgaagagtgttgacgcgtcgtgaagtcgggacgagg
tagggagtgattatgcttcgggatgagtagtacatacatatccaagccctaccgtgctgaagagtgttgacgcgtcgaagtaatgtcggtcgcctttgcaag
gcattccag[ATGCTGCTTCGTCATCCGACTCGTTGCCCGAGCGATCATCTACCGCGACCATTAGGAGTTGGATCAGGAGACGCGCCCTCAGTTACAAGGAGCCTACGACGAGTTCCGGACTACC
TGGCGAGTGGTCCTTGCCCGAGCGATCATCTACCGCGACCATTAGGAGTTGGATCAGGAGACGCGCCCTCAGTTACAAGGAGCCTACGACGAGTTCCGGACTACC
TGCGGGCGAGCGTCCTTAATCTCGCGCTCTATTCTCTGGAGGATTGTCTCAGGATCTGAAGCCGTCGCCTTACGAGGCGTTGTTTGGATCAGGAGCAGCGATAC
AAAGGCGCGGCCGCGTTTCTGACCACCACCGGCCTGGGCCGCTGGCCGACGCATGCCATACCGGCTGCTCTATGCCGCCATAGCCCCATGGCCATGGCCAGCGGTGC
TTCTGGACCAGCCGCAGCGGCCACCAACCAGCCCTGGCCGCTGCCGTCTGCGGACGTTCCGGACTGCGAGACTGCGAGACTTCCGCAAGTCGGCCAAGTGTA
CGTACATATGCCTGCAGCGGCGGTGAGGAGTGCTAACGTCTGTCCCAG[CCCTGCCAGTCATGCATGGATCGGTCATGCACGAGGCCTGCCTGGAGTCATGGCGGCCCTTCAAGC
GCTGCCTCGCTCCGAGATACGTCCAGATCTACACTTCTTTTCTCTATCGGCTGCATGGACGTCCCGTCGCGATGCCAGCAGCGAGGCTCTGCGGCGG
GACTTGGATCTTCTTTTCATGCAGCTACGCGCATCGTCCCAGGATGTTGTGCAGTGCGCCGAGGATGCGGAGTTGTCCAGCCTGACCGTTTC
CTCCGCGGCCGCTTCGTCGTTTCTCGTTTGCTCGTTGGCAGGCGCCGTCGCCGCGATCCGGCCTCGAGAGCGCTTCGCTCGCGTCGGGCA
CTCGGGGCTTTGGTGTGGAATTGGCCAGTGCGAGCAGTGA]gacgttgtggaaagtgatgatgatgtattcagctatctagctactctacacatgctatccacacatggcacaacgaggcatag
gtattatcgtgcgctaggcacgtgactggaacagatatcccctcgcaggatataaaggtagaaaaaggattgaattgaaaaaggtagaaaaggattgaattgaattaaagctatctcttcttattataaata

Figure 10

```
PP02          1   ------------------------------------------------            0
Om(KIM95229)  1   MERANFTLLVLLVPVNLFIASQTPKRFRFLYAVFQLGLHFAIVLLVPPG           50

PP02          1   ---------------MLVIERDIYADYYEL---DDK--------------          18
                                 . : : : . :.: . : . :||
Om(KIM95229) 51   SVPSSDYTFGTTFYSVLAAFNFFFCDPYEEHWQIAPEEDKIDQGRDRSR          100

PP02         19   EKTPVRYRSLSSWGKWEWCLAHCFSARGIGFSWAIPHLPEAMPSNTTIRD           68
                  : |: . |:  :||::|    | | |.:| |:|:||.:  |  .:
Om(KIM95229) 101  QSSPVYKYKDLDLRASVLWCISNAFALRGIGWNWRIPHLPGPFTRGISRVP         150

PP02         69   YLRASALNLGWLYLVQDLGRSLLSADLFAHEGVGASDTKGG---------          109
                  ||| .: |  : : | :|      | | : : :  .:  |    | |
Om(KIM95229) 151  YLIDVGTTLLKLYLLHDFSATLL------EKV----TLGGQLPLENIRL         189

PP02         110  -ARFLTVYSLGIGALLNIDMPYRAVCAMGMASGCFWTRPHEINRPAVGRWR         158
                   . :.:.|.|:.:: :|::      :|:|  .||: :: : :|: |.  :
Om(KIM95229) 190  DLRTVAVVSFAVSSITLIEFGYQIICFAGAATGLFWTRFQDNHPVIGSVY         239

PP02         159  DAWTLRRFWGRVWHQTFRKPWQSIGQWIAWEVMRALKGSLVSRYVQVYTS         208
                  :  || . |.|||| .: ||                    : :: :.
Om(KIM95229) 240  EGYTIGRFWGRVWHQNMRR---APGKVLAQKVLHVKRGGLVSRYVQSYTA         286

PP02         209  FLLSALMHVAAARMADPH---RRSCAGTWIFFLMQANGIVAEDVVQWAGK         255
                  | :: .::  : :: :|         | | :|:: :.:..    |   :
Om(KIM95229) 287  FFLSGVYHYIGAKSSLPHEQLNRTC----W-FFLLQPNLMLIEDFALWFGK         332

PP02         256  -KIGMRESSSLITRFLGRAWLCWFAWTAPWFFGDIADVGLI-RLETFPLS         303
                  |. |:                  |: :::|: |  : :
Om(KIM95229) 333  EKLGLK--SPRWTCLGYVWTFVMLTVTAAGFVJDCIRHQLVPPTSAFSFS         380

PP02         304  VTRGLWNRQWKM         315
                  . . .|.: |:
Om(KIM95229) 381  LA-ALLIQKWEL         391
```

Figure 11

Figure 13

```
JtmD          1 MGTCSTRVGETPSKPADVTPPEPWQALAQGLGFANENERYWWSKLAPLAG   50
                  .::.   ..::..:|||::||||||::||||||||::::||
Ou(KOM22681)  1 ------MAASPTY-ENGTPSQPWQALAQGLGYVNQDEQYWWSKVGPLAQ.   42

JtmD         51 KMMKWGQYSTPEQYRVLAFIHAYIVPSCGFRPGDGGDLFWKVFLNYDCTP  100
                :.::..|||||:|||||||:.||.|.:|.|:|:.|:|:||:.:|||||:|
Ou(KOM22681) 43 RLMEWARYSTPERYRVLAFIYTYIVPACGPKPDDNGQVFWKTYINYDCTP   92

JtmD        101 IQLSLNYHDGKMTLRTAHIPISNISGTAEDPINQKAAIDAMVRQQQVLPS  150
                ||||||:|||.:|.||:|||||||||||||||||:.|::|:||:.|||||
Ou(KOM22681) 93 IQLSLNFHDKKVTFRTANISSSDISGTAKDPINQQAAVDAMIKQKRVLPS  142

JtmD        151 QDMRWFNHFVSKLFLDRDTAATLKAKVDEFQIRQGVQCMLSHDFPDNH-Q  200
                |:|||||||.||||||||:|||||:||||||||.||||||||||||.:|
Ou(KOM22681)143 QNMRWFNHFMSKLFLEPEAAAALKAKADEFQIRNGVQCMLSHDFPNSQVQ  192

JtmD        201 CKLAFASHWKSIATGLDKEEVIWDAILGLGDDVIPYKPVLAMLQQYSTSK  250
                ||:|||:.|.||..||||:||:||||||||:||||||..|||||||||
Ou(KOM22681)193 CKAFFAPNWKAFATGIEMKDVIWDAIMALGDDILPYKSGLAILDRFTTSA  242

JtmD        251 SAAAAGAHPIFFAIDSVLKDDYTSSRIKIYFVTHRTAFNVMVDIYTLGGL  300
                |||||||.|||||||:|:||||:||||||||..|.||||||:||||||
Ou(KOM22681)243 SAAAAGAVPVCFAFDSVLEGDYKNSRIKITYYATLRTAFDVMVEIYTLGGL  292

JtmD        301 IMGPCIERGTQALRTLWKAVLNVPEGWPDDKDLPINPNGCAAVIFNFEVR  350
                :.||:|:.|:|||:||.||||||.|||.|:|.||||::|::||||:|||
Ou(KOM22681)293 LTGPEMEKGVQALRMLWNAVVNIPDGWPDDTDLPANPHRFAAVLFNFETR  342

JtmD        351 PGAEFPAPKIYLPAHYYGRPDLEIADGMDRFFLSQGWDGIYPGYKKNYLK  400
                .|||:|||||||||||||||:|||:|||||||.||||||||||||||:|
Ou(KOM22681)343 HGAELPVPQIYIPAHYYGRSDLEIADGVDRFFQSQGLDADYPPYKENYTK  392

JtmD        401 CLSVIVAPGLLSLCFWLTVR  420
                ||
Ou(KOM22681)393 CL------------------  394
```

Figure 14

Figure 16

```
JtmO         1  MGDPLPGNTRDCLSRNMRDSSTEKLPILWRTDS-PLNQYDEARCRVFNGR      49
                ::        :           :::  ::::::  ::::  :
Ew(KOS22754) 1  MAD------LPIIWRSDTESAAKYEEARCRIFNIR                    29

JtmO         50 RPEHFPRAIVQAT-LDHIVAAVRLAVESAAPVAVRSGGHSLSCWTMRHDA     99
                ||||||||||||  |||||||| |:       ||||||:|| || ||||
Ew(KOS22754) 30 RPEHFPRAIVKAT-LEHTVAAVKLAAEQGVRVVARSGGHGLSAWTLRHNA     79

JtmO        100 ILIDLKDFSYLSYDEETHQVQASPSTLTGELLEFLAQKQRFFPVGHSGGI    149
                ||||| |:  : : :::|   |||:|  || |::|| :::|||  |||:
Ew(KOS22754) 80 ILIDLQNFKHMSYDEEKNEA2VSPSTLAEELLDFLAERRKFFPAGHTGDI    129

JtmO        150 GLGGYLLQAG-GLNCRGYGYACESVSGIDIVTADGLIKHCDKEENADLYW    199
                |||||||:|| ||:||||||||| |||||||| ||:|| :|:|||||||
Ew(KOS22754)130 GLGGYLLQGG-GLSCRGYGYACEYVTGVDVVTAEGDVVHADENENADLYW    179

JtmO        200 AARGAGEFPAIV-RFYLETRPM-PVCNRSTYIWPATMYDQVFPWLDRVS     248
                |||||||||||| ||||| :| |  ||:||:||| ||  ::|:   |
Ew(KOS22754)180 AARGAGEFPAIV-RFYLKTIPLQPVAKGCRYIWPAVMYDA-FSWIDKIS     229

JtmO        249 SSCPCPQPSSRGFKLLFTLDENVEVGFGFTVPQLNQPGLHVLATAFPGDS    298
                ::    :       |
Ew(KOS22754)230 AS-----------LDEHVDPSVFGFMIPGINQPGLMFSASVFPAQT      263

JtmO        299 DEDTRRMLTPFID-HPPGAIHAQDFVATDFASDYVLDKTVLPQGARYFTD    348
                :::  | | |:|  ||||:||::|| ||::|:|||:|||  |: ||:||
Ew(KOS22754)264 EEEARRKLAPLVE-HPPGAMVAEDFVDSSITTVYAGSRQEFNPPGCRYFTD   313

JtmO        349 SVFLKPGTDLVVACKDMFTGLKHPRALAYWQPMKFATARTLPDMAMSIHS    398
                ||||||||||||| :|:||||:||:|||||||:|  |||:::  ::|
Ew(KOS22754)314 SVFLKPGTDVVEACRHMFTQIPFFRGLAYWQPLRISPARKQPDMALSIQS    363

JtmO        399 DHYVSLLGIYDDSAQDDEQTSWIVDYMRKLEPFVLGTFVGDAHVLERPSN    448
                :|||||| |  :|||    :|:|:| ::||| ||   :|   ::|
Ew(KOS22754)364 EHYVSLLAVYDNEAEDEAQTEWVIEGIRKLEPQIHGTFIADAHPEMRTSN    413

JtmO        449 YWSEEAKERVLIRVGKKWDPSGRIRGMLLSDS        479
                |||||| ::||:||| ||| ::: : ::
Ew(KOS22754)414 YWSEEATARLAAVGSKWDPKGRITGIVVRQE        444
```

Figure 17

CTACCTTACTGTTAGCCAAGGGCAAAGGGAAAGAAGGCCAGGGGCAACAAGAACAGACAA
GCACTTGAGGTAGTTTTTCTTATAGCCAGGGTAAATACCATCCCATCCCTGGCTCAGGAA
AAA*GCGGTCCATTCCATCAGCAATCTCCAAGTCGGGTCGGCCATAGTAATGGGCTGGGAG*
*GTAAATCTTAGGAGCCGGGAACTCGGCGCCAGGCCGGACCTCAAAGTTGAAGATGACTGC*
*CGCACAGCCATT*GGGGTTGATGGGTAGATCCTTATCGTCTGGCCACCCCTCGGGAACATT
GAGCACGGCCTTCCAGAGTGTCCTCAAGGCCTGCGTGCCCTTTTCAATACAAGGCCCCAT
TAGCAAACCACCTAGGGTATAGATGTCAACCATGACGTTAAAGGCAGTTCGGTGGGTAAC
AAAATAGATCTTGATACGTGAGCTTGTATAGTCGTCTTTGAGCACCGAGTCGATGGCGAA
AAAGATCGGATGTGCCCTGCAGCTGCGGCACTTTTGGACGTTGAGTATTGCTGGAGCAT
AGCGAGCACTGGCTTATACGGAATAACGTCGTCCCCTAACC<u>CCAAGATTGCATCCCAGAT</u>
<u>AACTTCCTCCTTATCAAGGCCAGTGGCGATAGACTTCCAGTGGGAGGCAAAGGCTAGCTT</u>
<u>ACACTGGATGTGATT</u>GTCGGGAAAGTCGTGGCTGAGCATGCACTGAACTCCCTGCCGGAT
CTGGAACTCGTCCACCTTGGCCTTGAGGGTGGCCGCCGTATCTCGATCCAGGAAGAGCTT
AGATACAAAGTGGTTAAACCAGCGCATGTCCTGGGACGGCAGGACCTGTTGCTGGCGGAC
CATGGCATCTATCGCAGCCTTCTGGTTAATGGGGTCTTCTGCTGTGCCGGAGATATTGCT
GATAGGTATATGAGCTGTCCGAAGCGTCATCTTCCCATCGTGGTAGTTGAGACTGAGCTG
GATAGGGGTGCAATCGTAGTTGAGAAACACCTTCCAGAACAGATCACCGCCATCCCCAGG
CCTTGGGCCACAGCTAGGGACAATATACGCGTGTATGAATGCCAGGACTCTGTACTGCTC
CGGCGTCGAGTACTGCCCCCACTTCATCATCTTGCCAGCCAGGGGGCAAGTTTGGACCA
CCAGTACCTCTCGTTCTCATTGGCGAACCCTAGACCCTGAGCTAGGGCCTGCCATGGCTC
AGGCGGCGTCACATCTGCTGGTTTCGATGGCGTCTCGCCTACGCGAGTGGAACAGGTGCC
CAT

Figure 21

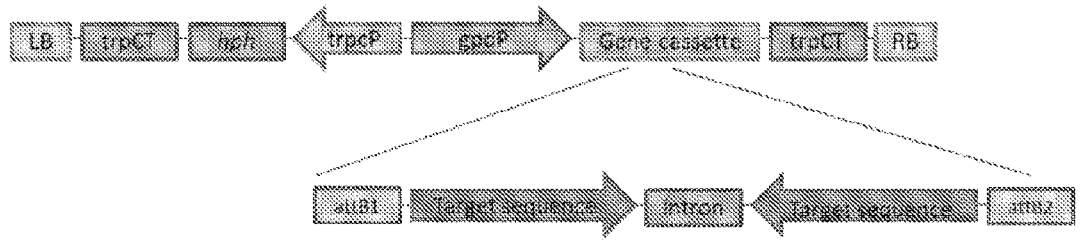

Figure 22

METABOLITE PRODUCTION IN ENDOPHYTES

FIELD OF THE INVENTION

The present invention relates to the biosynthesis of janthitrem compounds. In particular, the invention relates to genes encoding enzymes responsible for the synthesis of janthitrem and related constructs, vectors and methods.

BACKGROUND OF THE INVENTION

Endophytes reside in the tissues of living plants and offer a particularly diverse source of novel compounds and genes that may provide important benefits to society, and in particular to agriculture. Endophytes often form mutualistic relationships with their hosts, with the endophyte conferring increased fitness to the host, often through the production of defence compounds. At the same time, the host plant offers the benefits of a protected environment and nutriment to the endophyte. The plant provides nutrients for the endophyte and a means of dissemination through the seed. The endophyte protects the host from biotic (e.g. insect and mammalian herbivory) and abiotic stress (e.g. drought).

Important forage grasses perennial ryegrass and tall fescue are commonly found in association with fungal endophytes. Both beneficial and detrimental agronomic properties result from the association, including improved tolerance to water and nutrient stress and resistance to insect pests. Insect resistance is provided by specific metabolites produced by the endophyte, in particular loline alkaloids and peramine. Other metabolites produced by the endophyte, lolitrems and ergot alkaloids, are toxic to grazing animals and reduce herbivore feeding. These compounds can accumulate to high levels in plants where they act as potent feeding deterrents against a range of insect pests.

Janthitrems are a class of indole diterpenes, and are produced by a subgroup of endophytes. In 1980, an outbreak of ryegrass staggers syndrome led to the first identification of janthitrem alkaloids (Gallagher et al. 1980) Recent discoveries highlight the diversity of janthitrems; *P. janthinellum* isolates from Australia and New Zealand produce a wide range of janthitrems (janthitrem B, C, D, E, F and G).

Janthitrems are a class of indole diterpenes with structural similarity to lolitrem B (FIG. 1). The epoxy-janthitrems are a group of five compounds: three further structures isolated alongside epoxy-janthitrem I were assigned epoxy-janthitrem II [10-deacetyl-10,34-(3-methylbut-2-enyl acetal)]; epoxy-janthitrem III [10-deacetyl-34-O-(3-methylbut-2-enyl)]; and epoxy-janthitrem IV [34-O-(3-methylbut-2-enyl)], each of which are derivatives of epoxy-janthitrem I on the basis of LC-MS analysis. Epoxy-janthitrem I is the major janthitrem alkaloid produced by perennial ryegrass endophytes.

The presence of janthitrems in perennial ryegrass pastures provides superior protection against a wide range of important pasture pests. Recent discoveries have indicated that janthitrems can be tremorgenic in nature, similar to lolitrem B. Lolitrem B is known to be the main causative agent in ryegrass staggers. This is a condition in which animals grazing on endophyte infected pastures develop ataxia, tremors, and hypersensitivity to external stimuli. Like lolitrem B, janthitrem B can induce a tremorgenic response. Recent bioactivity studies of janthitrems A and B from *P. janthinellum* found these two compounds to be tremorgenic to mice and to have anti-insect activity to porina (*Wiseana cervinata*) larvae (Babu, 2009). Further, when purified, *Epichloë* endophyte derived janthitrems have been observed to exhibit bioprotective properties that provide an advantage to pasture.

Despite these useful properties, janthitrem alkaloids are not well understood when compared to other alkaloid groups synthesised by endophytes. There is an increasing need to further understand janthitrems and their biosynthesis, as this would provide information useful in manipulating janthitrem production.

It is an object of the present invention to overcome, or at least alleviate, one or more of the difficulties or deficiencies associated with the prior art.

SUMMARY OF THE INVENTION

In one aspect, the present invention provides a substantially purified or isolated nucleic acid or nucleic acid fragment encoding a gene involved in the biosynthesis of a janthitrem in an endophyte.

By 'nucleic acid' is meant a chain of nucleotides capable of genetic information. The term generally refers to genes or functionally active fragments or variants thereof and or other sequences in the genome of the organism that influence its phenotype. The term 'nucleic acid' includes DNA (such as cDNA or genomic DNA) and RNA (such as mRNA or microRNA) that is single- or double stranded, optionally containing synthetic, non-natural or altered nucleotide bases, synthetic nucleic acids and combinations thereof.

Nucleic acids according to the invention may be full-length genes or part thereof, and are also referred to as "nucleic acid fragments" and "nucleotide sequences" in this specification. For convenience, the expression "nucleic acid or nucleic acid fragment" is used to cover all of these.

By 'substantially purified' is meant that the nucleic acid is free of the genes, which, in the naturally-occurring genome of the organism from which the nucleic acid of the invention is derived, flank the nucleic acid. The term therefore includes, for example, a nucleic acid which is incorporated into a vector; into an autonomously replicating plasmid or virus; or into the genomic DNA of a prokaryote or eukaryote; or which exists as a separate molecule (e.g. a cDNA or a genomic or cDNA fragment produced by PCR or restriction endonuclease digestion) independent of other sequences. It also includes a nucleic acid which is part of a hybrid gene encoding additional polypeptide sequence. Preferably, the substantially purified nucleic acid is 90%, more preferably 95%, even more preferably 98% pure.

The term "isolated" means that the material is removed from its original environment (e.g. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

In a preferred embodiment of this aspect of the invention, the janthitrem producing endophyte is an *Epichloë* endophyte, in a more preferred embodiment the endophyte is from the taxa LpTG-3 or LpTG-4, and in an even more preferred embodiment the endophyte is selected from the group consisting of NEA12, AR37, 15310, 15311 and E1.

In a second aspect of the present invention there is provided substantially purified or isolated nucleic acid or nucleic acid fragment encoding a janthitrem biosynthesis polypeptide, or complementary or antisense to a sequence encoding a janthitrem biosynthesis polypeptide, said nucleic acid or nucleic acid fragment including a nucleotide sequence selected from the group consisting of (a) sequences shown in FIGS. 7, 10, 13 and 16 hereto (Sequence ID Nos 1, 2, 5, 6, 9, 10, 13 and 14); (b) complements of the sequences recited in (a); (c) sequences antisense to the sequences recited in (a) and (b); and (d) functionally active fragments and variants of the sequences recited in (a), (b) and (c) having at least approximately 80% identity to the relevant part of the sequences recited in (a), (b) and (c) and having a size of at least 20 nucleotides.

The present invention encompasses functionally active fragments and variants of the nucleic acids of the present invention. By 'functionally active' in relation to the nucleic acid is meant that the fragment or variant (such as an analogue, derivative or mutant) is capable of modulating janthitrem biosynthesis. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the above mentioned sequence to which the fragment or variant corresponds, more preferably at least approximately 90% identity, even more preferably at least approximately 95% identity, most preferably at least approximately 98% identity. Such functionally active variants and fragments include, for example, those having conservative nucleic acid changes.

Preferably the fragment has a size of at least 20 nucleotides, more preferably at least 50 nucleotides, more preferably at least 100 nucleotides, more preferably at least 200 nucleotides, more preferably at least 500 nucleotides.

By 'conservative nucleic acid changes' is meant nucleic acid substitutions that result in conservation of the amino acid in the encoded protein, due to the degeneracy of the genetic code. Such functionally active variants and fragments also include, for example, those having nucleic acid changes which result in conservative amino acid substitutions of one or more residues in the corresponding amino acid sequence.

By 'conservative amino acid substitutions' is meant the substitution of an amino acid by another one of the same class, the classes being as follows:

Nonpolar: Ala, Val, Leu, Ile, Pro, Met Phe, Trp

Uncharged polar: Gly, Ser, Thr, Cys, Tyr, Asn, Gln

Acidic: Asp, Glu

Basic: Lys, Arg, His

Other conservative amino acid substitutions may also be made as follows:

Aromatic: Phe, Tyr, His

Proton Donor: Asn, Gln, Lys, Arg, His, Trp

Proton Acceptor: Glu, Asp, Thr, Ser, Tyr, Asn, Gln

In a further aspect of the present invention, there is provided a genetic construct including a nucleic acid according to the present invention. In a preferred embodiment the genetic construct may include a chimeric sequence comprising a nucleic acid according to the present invention and a gene encoding a mediator or modulator janthitrem biosynthesis. Preferably, the gene encoding a mediator or modulator of janthitrem biosynthesis is exogenous, i.e. it does not naturally occur in combination with the nucleic acid according to the present invention.

The term "genetic construct" as used herein refers to an artificially assembled or isolated nucleic acid molecule which includes the gene of interest. Preferably the genetic construct is a recombinant nucleic acid molecule. In general a construct may include the gene or genes of interest, a marker gene which in some cases can also be the gene of interest and appropriate regulatory sequences. Preferably the marker gene is exogenous, i.e. it does not naturally occur in combination with the nucleic acid according to the present invention.

It should be appreciated that the inclusion of regulatory sequences in a construct is optional, for example, such sequences may not be required in situations where the regulatory sequences of a host cell are to be used. The term construct includes vectors but should not be seen as being limited thereto.

By a 'chimeric sequence' is meant a hybrid produced by recombinant means through expression of a fusion gene including two or more linked nucleic acids which originally encoded separate proteins, or functionally active fragments or variants thereof.

By a 'fusion gene' is meant that two or more nucleic acids are linked in such a way as to permit expression of the fusion protein, preferably as a translational fusion. This typically involves removal of the stop codon from a nucleic acid sequence coding for a first protein, then appending the nucleic acid sequence of a second protein in frame. The fusion gene is then expressed by a cell as a single protein. The protein may be engineered to include the full sequence of both original proteins, or a functionally active fragment or variant of either or both.

In a preferred embodiment, the genetic construct according to the present invention may be a vector.

The vector may be of any suitable type and may be viral or non-viral. The vector may be an expression vector. Such vectors include chromosomal, non-chromosomal and synthetic nucleic acid sequences, e.g. derivatives of plant viruses; bacterial plasmids; derivatives of the Ti plasmid from *Agrobacterium tumefaciens*; derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable or integrative or viable in the target cell.

In a preferred embodiment of this aspect of the invention, the genetic construct may further include a promoter and a terminator; said promoter, gene and terminator being operatively linked.

By a 'promoter' is meant a nucleic acid sequence sufficient to direct transcription of an operatively linked nucleic acid sequence.

By 'operatively linked' is meant that the nucleic acid(s) and a regulatory sequence, such as a promoter, are linked in such a way as to permit expression of said nucleic acid under appropriate conditions, for example when appropriate molecules such as transcriptional activator proteins are bound to the regulatory sequence. Preferably an operatively linked promoter is upstream of the associated nucleic acid.

By 'upstream' is meant in the 3'→5' direction along the nucleic acid.

The promoter and terminator may be of any suitable type and may be endogenous to the target cell or may be exogenous, provided that they are functional in the target cell. Preferably, the promoter and/or terminator is exogenous, i.e. it does not naturally occur in combination with the nucleic acid according to the present invention.

A variety of terminators which may be employed in the genetic constructs of the present invention are also well known to those skilled in the art. The terminator may be from the same gene as the promoter sequence or a different gene. Particularly suitable terminators are polyadenylation signals, such as the (CaMV) 35S polyA and other terminators from the nopaline synthase (nos) and the octopine synthase (ocs) genes.

The genetic construct, in addition to the promoter, the gene and the terminator, may include further elements necessary for expression of the nucleic acid, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (nptII) gene, the hygromycin phosphotransferase (hph) gene, the phosphinothricin acetyltransferase (bar or pat) gene], and reporter genes [such as beta-glucuronidase (GUS) gene (gusA) and the green fluorescent protein (GFP) gene (gfp)]. The genetic construct may also contain a ribosome binding site for translation initiation. The genetic construct may also include appropriate sequences for amplifying expression.

Those skilled in the art will appreciate that the various components of the genetic construct are operably linked, so as to result in expression of said nucleic acid. Techniques for operably linking the components of the genetic construct of the present invention are well known to those skilled in the art. Such techniques include the use of linkers, such as synthetic linkers, for example including one or more restriction enzyme sites.

Preferably, the genetic construct is substantially purified or isolated.

By 'substantially purified' is meant that the genetic construct is free of the genes, which, in the naturally-occurring genome of the organism from which the nucleic acid or promoter of the invention is derived, flank the nucleic acid or promoter. The term therefore includes, for example, a genetic construct which is incorporated into a vector; into an autonomously replicating plasmid or virus; or into the genomic DNA of a prokaryote or eukaryote; or which exists as a separate molecule (e.g. a cDNA or a genomic or cDNA fragment produced by PCR or restriction endonuclease digestion) independent of other sequences. It also includes a genetic construct which is part of a hybrid gene encoding additional polypeptide sequence.

Preferably, the substantially purified genetic construct is at least approximately 90% pure, more preferably at least approximately 95% pure, even more preferably at least approximately 98% pure.

The term "isolated" means that the material is removed from its original environment (e.g. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

As an alternative to use of a selectable marker gene to provide a phenotypic trait for selection of transformed host cells, the presence of the genetic construct in transformed cells may be determined by other techniques well known in the art, such as PCR (polymerase chain reaction), Southern blot hybridisation analysis, histochemical assays (e.g. GUS assays), thin layer chromatography (TLC), northern and western blot hybridisation analyses.

The genetic constructs of the present invention may be introduced into plants or fungi by any suitable technique. Techniques for incorporating the genetic constructs of the present invention into plant cells or fungal cells (for example by transduction, transfection, transformation or gene targeting) are well known to those skilled in the art. Such techniques include *Agrobacterium*-mediated introduction, *Rhizobium*-mediated introduction, electroporation to tissues, cells and protoplasts, protoplast fusion, injection into reproductive organs, injection into immature embryos and high velocity projectile introduction to cells, tissues, calli, immature and mature embryos, biolistic transformation, Whiskers transformation, and combinations thereof. The choice of technique will depend largely on the type of plant or fungus to be transformed, and may be readily determined by an appropriately skilled person. For transformation of protoplasts, PEG-mediated transformation is particularly preferred. For transformation of fungi PEG-mediated transformation and electroporation of protoplasts and *Agrobacterium*-mediated introduction of hyphal explants are particularly preferred.

Cells incorporating the genetic constructs of the present invention may be selected, as described below, and then cultured in an appropriate medium to regenerate transformed plants or fungi, using techniques well known in the art. The culture conditions, such as temperature, pH and the like, will be apparent to the person skilled in the art. The resulting plants may be reproduced, either sexually or asexually, using methods well known in the art, to produce successive generations of transformed plants or fungi.

Accordingly, in a further aspect of the present invention there is provided a transgenic plant cell, plant, plant seed or other plant part, or a transgenic fungus, fungal cell or other fungal part, capable of producing janthitrem in greater quantities than an untransformed control plant cell, plant, plant seed or other plant part, or an untransformed fungus, fungal cell or other fungal part.

In a preferred embodiment the a transgenic plant cell, plant, plant seed or other plant part or the transgenic fungus, fungal cell or other fungal part has an increase in the quantity of janthitrem produced of at least approximately 10%, more preferably at least approximately 20%, more preferably at least approximately 30%, more preferably at least approximately 40% relative to the untransformed control.

For example, the quantity of janthitrem may be increased by between approximately 10% and 300%, more preferably between approximately 20% and 200%, more preferably between approximately 30% and 100%, more preferably between approximately 40% and 80% relative to the untransformed control.

Preferably the transgenic plant cell, plant, plant seed or other plant part or the transgenic fungus, fungal cell or other fungal part includes a nucleic acid, genetic construct or vector according to the present invention. Preferably the transgenic plant cell, plant, plant seed or other plant part, or the transgenic fungus, fungal cell or other fungal part, is produced by a method according to the present invention.

The present invention also provides a transgenic plant, plant seed or other plant part, or a transgenic fungus, fungal cell or other fungal part, derived from a plant or fungal cell of the present invention and including a nucleic acid, genetic construct or vector of the present invention.

The present invention also provides a transgenic plant, plant seed or other plant part, or a transgenic fungus, fungal cell or other fungal part, derived from a plant or fungus of the present invention and including a nucleic acid, genetic construct or vector of the present invention.

By 'plant cell' is meant any self-propagating cell bounded by a semi-permeable membrane and containing a plastid. Such a cell also requires a cell wall if further propagation is desired. Plant cell, as used herein includes, without limitation, algae, cyanobacteria, seeds suspension cultures, embryos, meristematic regions, callus tissue, leaves, roots, shoots, gametophytes, sporophytes, pollen and microspores.

By 'fungal cell' is meant any cell of a fungus. The term 'fungus' refers to whole fungi, fungal organs and tissues (e.g., asci, hyphae, pseudohyphae, rhizoid, sclerotia, sterigmata, spores, sporodochia, sporangia, synnemata, conidia, ascostroma, cleistothecia, mycelia, perithecia, basidia and the like), spores, fungal cells and the progeny thereof. Fungi may either exist as single cells or make up a multicellular body called a mycelium, which consists of filaments known as hyphae. Most fungal cells are multinucleate and have cell walls, composed chiefly of chitin.

By 'transgenic' is meant any cell which includes a DNA sequence which is inserted by artifice into a cell and becomes part of the genome of the organism which develops from that cell.

In a further aspect, the present invention provides a method of modifying janthitrem biosynthesis in an endophyte, said method including introducing into said endophyte an effective amount of a nucleic acid or nucleic acid fragment or a construct as hereinbefore described. The present invention also provides an endophyte including (e.g. transformed with) a nucleic acid or nucleic acid fragment or a construct as hereinbefore described. The nucleic acid, nucleic acid fragment or construct may be introduced into the endophyte by any suitable method as hereinbefore described.

In a further aspect, the present invention provides a plant inoculated with an endophyte as hereinbefore described, said plant comprising an endophyte-free host plant stably infected with said endophyte. Preferably the plant is one in which the endophyte does not naturally occur.

Preferably, the plant is infected with the endophyte by a method selected from the group consisting of inoculation, breeding, crossing, hybridization and combinations thereof.

In a preferred embodiment, the plant may be infected by isogenic inoculation. This has the advantage that phenotypic effects of endophytes may be assessed in the absence of host-specific genetic effects. More particularly, multiple inoculations of endophytes may be made in plant germplasm, and plantlets regenerated in culture before transfer to soil.

The identification of an endophyte of the opposite mating-type that is highly compatible and stable in planta provides a means for molecular breeding of endophytes for perennial ryegrass. Preferably the plant may be infected by hyper-inoculation.

Hyphal fusion between endophyte strains of the opposite mating-type provides a means for delivery of favourable traits into the host plant, preferably via hyper-inoculation. Such strains are preferably selected from the group including an endophyte strain that exhibits the favourable characteristics of high inoculation frequency and high compatibility with a wide range of germplasm, preferably elite perennial ryegrass and/or tall fescue host germplasm and an endophyte that exhibits a low inoculation frequency and low compatibility, but has a highly favourable alkaloid toxin profile.

It has generally been assumed that interactions between endophyte taxa and host grasses will be species specific. Applicants have surprisingly found that endophyte from tall fescue may be used to deliver favourable traits to ryegrasses, such as perennial ryegrass.

In a further aspect, the present invention provides a plant, plant seed or other plant part derived from a plant of the present invention and stably infected with an endophyte of the present invention.

Preferably, the plant cell, plant, plant seed or other plant part is a grass, more preferably a forage, turf or bioenergy grass, such as those of the genera *Lolium* and *Festuca*, including *L. perenne* and *L. arundinaceum.*

By 'plant cell' is meant any self-propagating cell bounded by a semi-permeable membrane and containing plastid. Such a cell also required a cell wall if further propagation is desired. Plant cell, as used herein includes, without limitation, seeds suspension cultures, embryos, meristematic regions, callus tissue, leaves, roots, shoots, gametophytes, sporophytes, pollen and microspores.

In a further aspect, the present invention provides use of an endophyte as hereinbefore described to produce a plant stably infected with said endophyte.

In a still further aspect, the present invention provides a substantially purified or isolated polypeptide involved in janthitrem biosynthesis in an endophyte.

In a preferred embodiment, the present invention provides a substantially purified or isolated janthitrem biosynthesis polypeptide including an amino acid sequence selected from the group consisting of (a) sequences shown in FIGS. 8, 11, 14 and 17 (Sequence ID Nos 3, 4, 7, 8 11, 12, 15 and 16); and (b) functionally active fragments and variants of the sequences recited in (a) having at least approximately 80% identity with the relevant part of the sequences recited in (a) and having a size of at least 20 amino acids.

The present invention encompasses functionally active fragments and variants of the polypeptides of the present invention. By 'functionally active' in this context is meant that the fragment or variant has one or more of the biological properties of the corresponding protein from which the fragment or variant is derived. Additions, deletions, substitutions and derivatizations of one or more of the amino acids are contemplated so long as the modifications do not result in loss of functional activity of the fragment or variant. Preferably the fragment or variant has at least approximately 80% identity to the relevant part of the above mentioned sequence to which the fragment or variant corresponds, more preferably at least approximately 90% identity, more preferably at least approximately 95% identity, most preferably at least approximately 98% identity. Such functionally active variants and fragments include, for example, those having conservative amino acid substitutions of one or more residues in the corresponding amino acid sequence.

By 'conservative amino acid substitutions' is meant the substitution of an amino acid by another one of the same class, the classes being as follows:

Nonpolar: Ala, Val, Leu, Ile, Pro, Met Phe, Trp

Uncharged polar: Gly, Ser, Thr, Cys, Tyr, Asn, Gln

Acidic: Asp, Glu

Basic: Lys, Arg, His

Other conservative amino acid substitutions may also be made as follows:

Aromatic: Phe, Tyr, His

Proton Donor: Asn, Gln, Lys, Arg, His, Trp

Proton Acceptor: Glu, Asp, Thr, Ser, Tyr, Asn, Gln

Preferably the fragment has a size of at least 10 amino acids, more preferably at least 20 amino acids, more preferably at least 50 amino acids, more preferably at least 100 amino acids, more preferably at least 200 amino acids.

In a further embodiment of this aspect of the invention, there is provided a polypeptide recombinantly produced from a nucleic acid or nucleic acid fragment according to the present invention. Techniques for recombinantly producing polypeptides are known to those skilled in the art.

Availability of the nucleotide sequences of the present invention and deduced amino acid sequences facilitates immunological screening of cDNA expression libraries. Synthetic peptides representing portions of the instant amino acid sequences may be synthesized. These peptides may be used to immunise animals to produce polyclonal or monoclonal antibodies with specificity for peptides and/or proteins including the amino acid sequences. These antibodies may be then used to screen cDNA expression libraries to isolate full-length cDNA clones of interest.

The present invention will now be more fully described with reference to the accompanying Examples and drawings. It should be understood, however, that the description following is illustrative only and should not be taken in any way as a restriction on the generality of the invention described above.

BRIEF DESCRIPTION OF THE DRAWINGS/FIGURES

In the Figures:

FIG. 1: Epoxy-janthitrem I and Lolitrem B. Epoxy-janthitrem I is a paxilline-like indole diterpene that exhibits structural similarity to lolitrem B. Structure, chemical formula ($C_{39}H_{51}NO_7$) and exact mass (645.3665) of 11,12-epoxyjanthitrem G (epoxy-janthitrem I) from Tapper et al. 2004.

FIG. 2: UPGMA phenogram of genetic relationships among endophytes in ryegrass accessions of diverse origins in relation to reference *Epichloë* species. Genetic identity was measured across 18 SSR loci using the Dice coefficient (Kaur et al, 2015). LpTG-3 and LpTG-4 endophyte strains are genetically distinct from other asexual *Epichloë* identified including *Epichloë festucae* var. *lolii* and LpTG-2 (Hettiarachchige et al. 2015).

FIG. 3: Genome survey sequence analysis was used to determine the presence/absence profiles of the genes responsible for peramine, ergovaline and lolitrem B biosynthesis in endophyte strains representing each of the four taxa observed to form associations with perennial ryegrass (*Epichloë festucae* var. *lolii*, LpTG-2, LpTG-3 and LpTG-4). Strains that do not produce lolitrem B have a deletion in the third (ItmE-ItmJ) lolitrem B gene cluster. Adapted from Davidson et al. 2012.

FIG. 4: NEA12 PacBio contig 3 is 247 475 bp in length and has 13 predicted and known genes in four clusters. Cluster 1 (ItmG, ItmS, ItmM, ItmK), Cluster 2 (ItmP, ItmQ, ItmF, ItmC, ItmB), Cluster 3 (PP01, PP02) and Cluster 4 (jtmD and jtmO). Light grey arrows display predicted and known genes and their orientation. The locations of the pks pseudogene, transposase with a MULE domain (PP03), Helitron helicase-like transposable element (TE), and three AT-rich regions are also shown. PP=predicted protein; TE=transposable element; ip=pseudogene.

Figure 5:
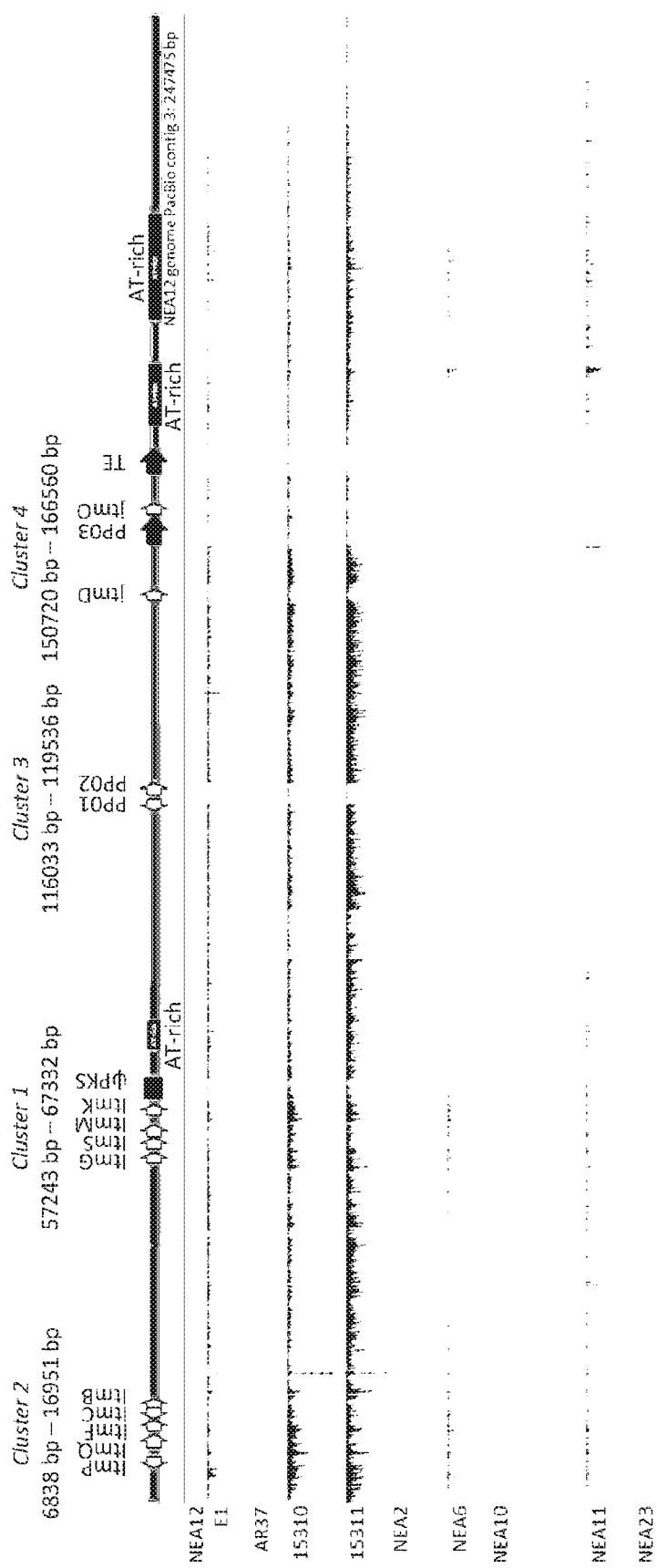

FIG. 5: Genomes of representative strains of *Epichloë* sp. endophytes from 4 taxa *Epichloë festucae* var. *lolii* (NEA2, NEA6, NEA10), LpTG-2 (NEA11), LpTG-3 (NEA12, AR37, 15310, 15311), LpTG-4 (E1) and FaTG-3 (NEA23) were mapped to NEA12 PacBio contig 3. A c. 177436 bp region (c.70039 bp 247475 bp) of the genome unique to janthitrem producing taxa LpTG-3 and LpTG-4 was identified. Within this region there are two gene clusters containing candidate genes (PP01, PP02, jtmD and jtmJ) predicted to be associated with janthitrem biosynthesis in *Epichloë* endophytes. Endophyte strains from the taxa LpTG-3 and LpTG-4 all contain candidate genes for janthitrem biosynthesis, while for endophytes from *Epichloë festucae* var. *lolii*, LpTG-2 and FaTG-3 this region is absent. DNA reads generated using Illumina sequencing technology were mapped with Gydle 'nuclear' aligner version 3.2.1. Reads were mapped with settings: 1 50 (length of overlap); s 25 (sensitivity); k 13 (kmer length); m 6 (maximum number of mis-matches); F 3 (filter settings). Alignments were visualised with Gydle program Vision version 2.6.14.

Figure 6:
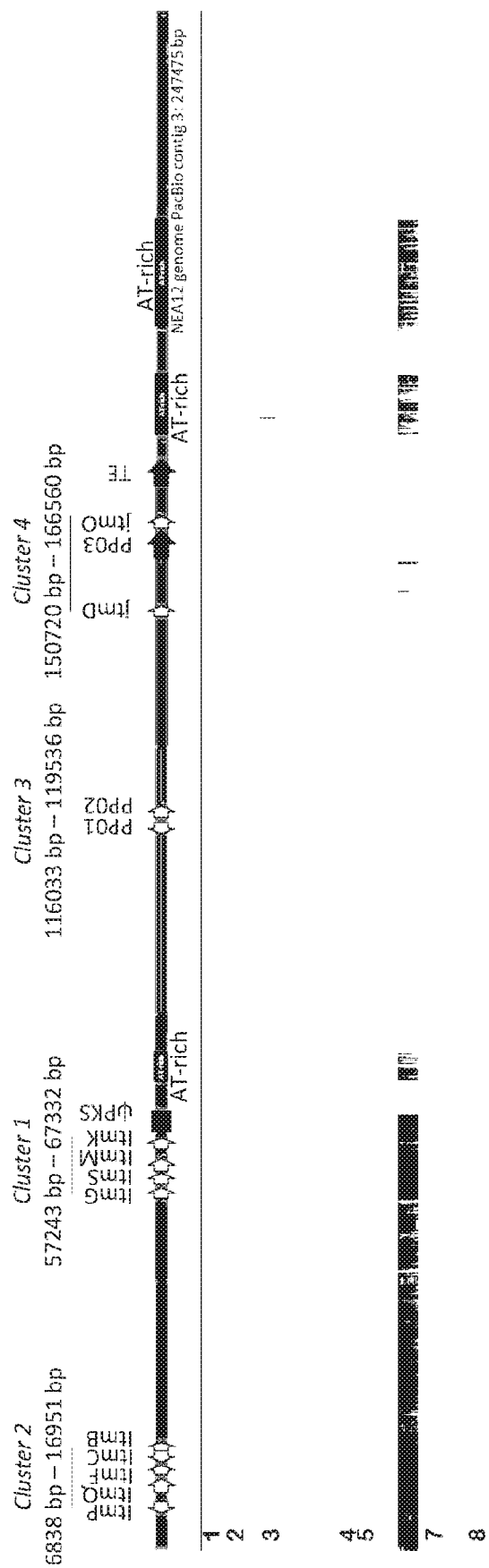

FIG. 6: In planta expression of NEA12 genome PacBio contig 3 genes. Genomes of representative strains of *Epichloë* sp. endophytes from LpTG-3 (AR37) and *Epichloë festucae* var. *lolii* (SE) were mapped to the 247475 bp NEA12 PacBio contig 3. In planta expression of candidate genes for janthitrem biosynthesis in LpTG-3, LpTG-4 and *Epichloë festucae* var. *lolii* was determined using RNA-seq analysis of perennial ryegrass-endophyte association transcriptome data (refer to key below). DNA and RNA reads were mapped with Gydle 'nuclear' aligner version 3.2.1. Reads were mapped with settings:150 (length of overlap); s 25 (sensitivity); k 13 (kmer length); m 6 (maximum number of mis-matches); F 3 (filter settings). Alignments were visualised with Gydle program Vision version 2.6.14. Expression of Cluster 2 (ltmP, ltmQ, ltmF, ltmC, ltmB), Cluster 1 (ltmG, ltmS, ltmM, ltmK), Cluster 3 (PP01, PP02) and Cluster 4 (jtmD and jtmO) genes was observed for endophyte strains NEA12 and E1 in planta. Cluster 3 and Cluster 4 genes are not present in the *Epichloë festucae* var. *lolii* (SE) genome, expression of these genes was not observed by SE in planta.

Key to FIG. 6

| Row | Genome/Transcriptome | Taxon (Strain) | Experiment | Treatment |
|---|---|---|---|---|
| 1 | Genome | LpTG-3 (AR37) | genome survey sequence analysis | n.a. |
| 2 | In planta transcriptome | LpTG-3 (NEA12) | seedling growth and maturation | post imbibition (0 hours) |
| 3 | In planta transcriptome | LpTG-3 (NEA12) | seedling growth and maturation | 10 day old seedlings (10 days) |
| 4 | In planta transcriptome | LpTG-4 (E1) | transcriptome atlas | leaf |
| 5 | In planta transcriptome | LpTG-4 (E1) | transcriptome atlas | stigma |
| 6 | Genome | *Epichloë* festucae var. *lolii* (SE) | genome survey sequence analysis | n.a. |

| Row | Genome/Transcriptome | Taxon (Strain) | Experiment | Treatment |
|---|---|---|---|---|
| 7 | In planta transcriptome | *Epichloë festucae* var. *lolii* (SE) | seedling growth and maturation | post imbibition (0 hours) |
| 8 | In planta transcriptome | *Epichloë festucae* var. *lolii* (SE) | seedling growth and maturation | 10 day old seedling (10 days) |

FIG. 7: Nucleotide sequence for the PP01 gene (Sequence ID No 1). The coding sequence for the predicted PP01 protein is highlighted in grey (Sequence ID No 2). The complete nucleotide sequence for the PP01 gene was identified by mapping RNA reads from the in planta (Alto-NEA12) transcriptome data described in FIG. 6 followed by extraction of the DNA sequence from NEA12 PacBio contig 3. Nucleotides shown in lowercase were not observed in the analysis of the Alto-NEA12 transcriptome dataset.

FIG. 8: PP01 is predicted to be a cytochrome P450 monoxygenase 387 amino acids in length. Shown here is the alignment of predicted amino acid sequences for PP01 from LpTG-3 strain NEA12 (Sequence ID No 3.) and *Hirsutella minnesotensis* (KJZ77225 amino acids 3-379) (Sequence ID No 4). Protein identity: 258/387 (66.7%); Protein similarity: 304/387 (78.6%); Gaps: 10/387 (2.6%). Sequences were aligned using EMBOSS Needle.

Figure 9:
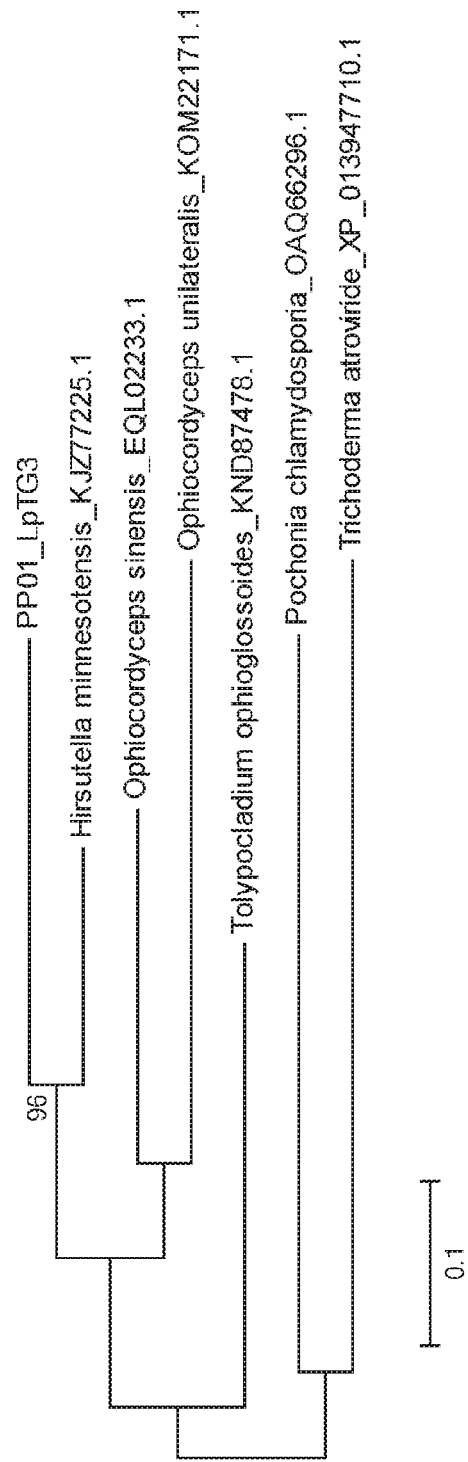

FIG. 9: Bootstrap consensus tree generated through Maximum Likelihood analysis of the predicted amino acid sequence of PP01 from LpTG-3 (NEA12) and the top 6 BLASTp hits in the NCBI database. Multiple alignment of complete predicted protein sequences was performed using ClustalW with default parameters. To construct tree topology, maximum likelihood (ML) was used as implemented in MEGA 6 with default parameters and 500 bootstrap replicates. Branches with bootstrap values of greater than 70% from 500 bootstrap replications are marked next to each branch. Genbank accession numbers for each protein sequence is provided in each tree diagram. PP01 exhibits sequence similarity to cytochrome P450 monoxygenases: KJZ77225.1 [68%; *Hirsutella minnesotensis* 3608]; EQL02233.1 [57%; *Ophiocordyceps sinensis* CO18]; KND87478.1 [53%; *Tolypocladium ophioglossoides* CBS 100239]; OAQ66296.1 [50%; *Pochonia chlamydosporia* 170]; KOM22171.1 [55%; *Ophiocordyceps unilateralis*]; XP_013947710.1 [48%; *Trichoderma atroviride* IMI 206040].

FIG. 10. Nucleotide sequence for the PP02 gene (Sequence ID No 5). The coding sequence for the predicted PP02 protein is highlighted in grey (Sequence ID No 6). Start (ATG) and stop (TGA) codon sequences are shown in bold. Untranslated 5' and 3' sequences are shown in lowercase. The complete nucleotide sequence for the PP02 gene was identified by mapping RNA reads from the in planta (Alto-NEA12) transcriptome data described in FIG. 6 followed by extraction of the DNA sequence from NEA12 PacBio contig 3.

FIG. 11. PP02 is predicted to be a membrane bound O-acyl transferase (MBOAT) protein 315 amino acids in length. Shown here is the alignment of predicted amino acid sequences for PP02 from LpTG-3 strain NEA12 (Sequence ID No 7) and *Oidiodendron maius* Zn (KIM95229) (Sequence ID No 8). Protein identity: 110/412 (26.7%); Protein similarity: 165/412 (40.0%); Gaps: 118/412 (28.6%). Within the predicted MBOAT domain (shown in bold) the two sequences exhibit protein identity of 42% (37/89) and protein similarity of 61% (54/89). Sequences were aligned using EMBOSS Needle.

Figure 12:
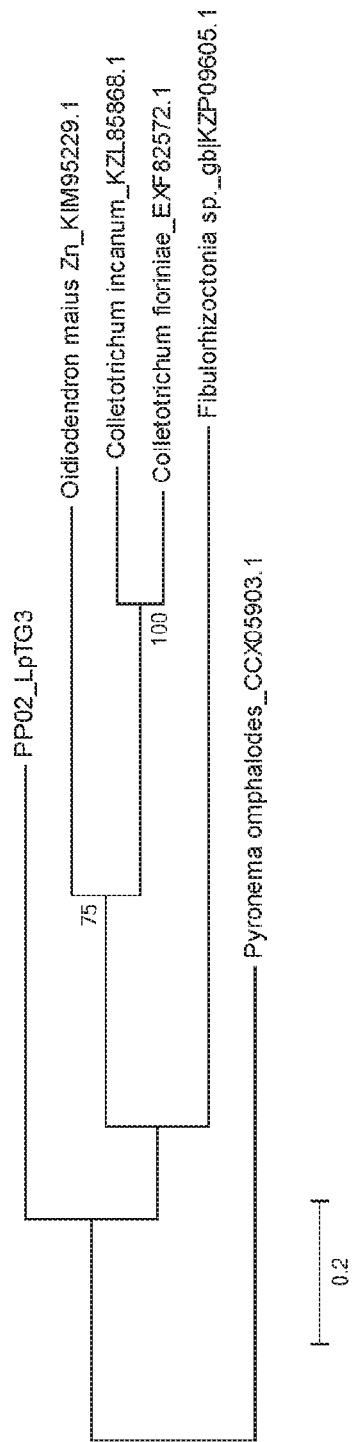

FIG. 12. Bootstrap consensus tree generated through Maximum Likelihood analysis of the predicted amino acid sequence of PP02 from LpTG-3 (NEA12) and the top 5 BLASTp hits in the NCBI database. Multiple alignment of complete predicted protein sequences was performed using ClustalW with default parameters. To construct tree topology, maximum likelihood (ML) was used as implemented in MEGA 6 with default parameters and 500 bootstrap replicates. Branches with bootstrap values of greater than 70% from 500 bootstrap replication are marked next to each branch. Genbank accession numbers for each protein sequence is provided in each tree diagram. PP02 exhibits sequence similarity to MBOAT proteins: KIM95229.1 [33%; *Oidiodendron maius* Zn]; KZL85868.1[30%; *Colletotrichum incanum*]; CCX05903.1 [30%; *Pyronema omphalodes* CBS 100304]; KZP09605.1 [29%; *Fibulorhizoctonia* sp. CBS 109695]; XP_007593790.1 [31%; *Colletotrichum fioriniae* PJ7].

Figure 13:
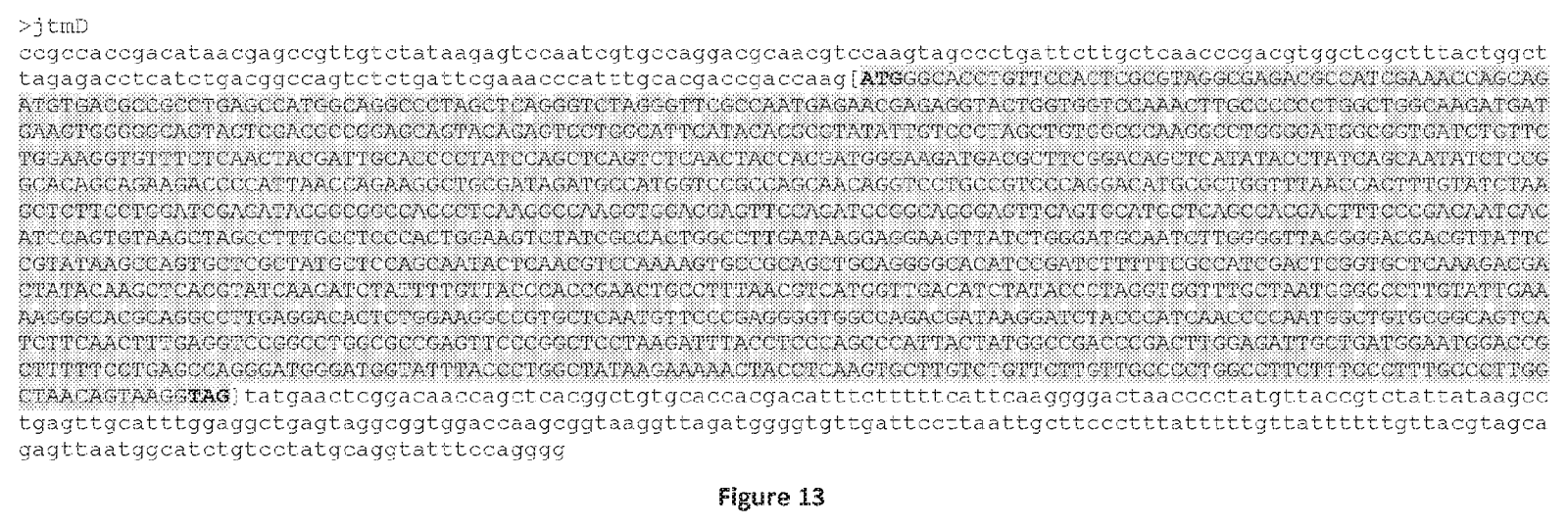

FIG. 13. Nucleotide sequence for the jtmD gene (Sequence ID No 9). The coding sequence for the predicted JtmD protein is highlighted in grey (Sequence ID No 10). Start (ATG) and stop (TGA) codon sequences are shown in bold. Untranslated 5' and 3' sequences are shown in lowercase. The complete nucleotide sequence for the jtmD gene was identified by mapping RNA reads from the in planta (Alto-NEA12) transcriptome data described in FIG. 6 followed by extraction of the DNA sequence from NEA12 PacBio contig 3.

FIG. 14. JtmD is predicted to be an aromatic prenyl transferase 420 amino acids in length (Sequence ID No 11). JtmD exhibits highest homology to a predicted protein from *Ophiocordyceps unilateralis* (KOM22681.1) (Sequence ID No 12). Protein identity: 264/420 (62.9%); Protein similarity: 334/420 (79.5%); Gaps: 26/420 (6.2%). Sequences were aligned using EMBOSS Needle.

Figure 15:
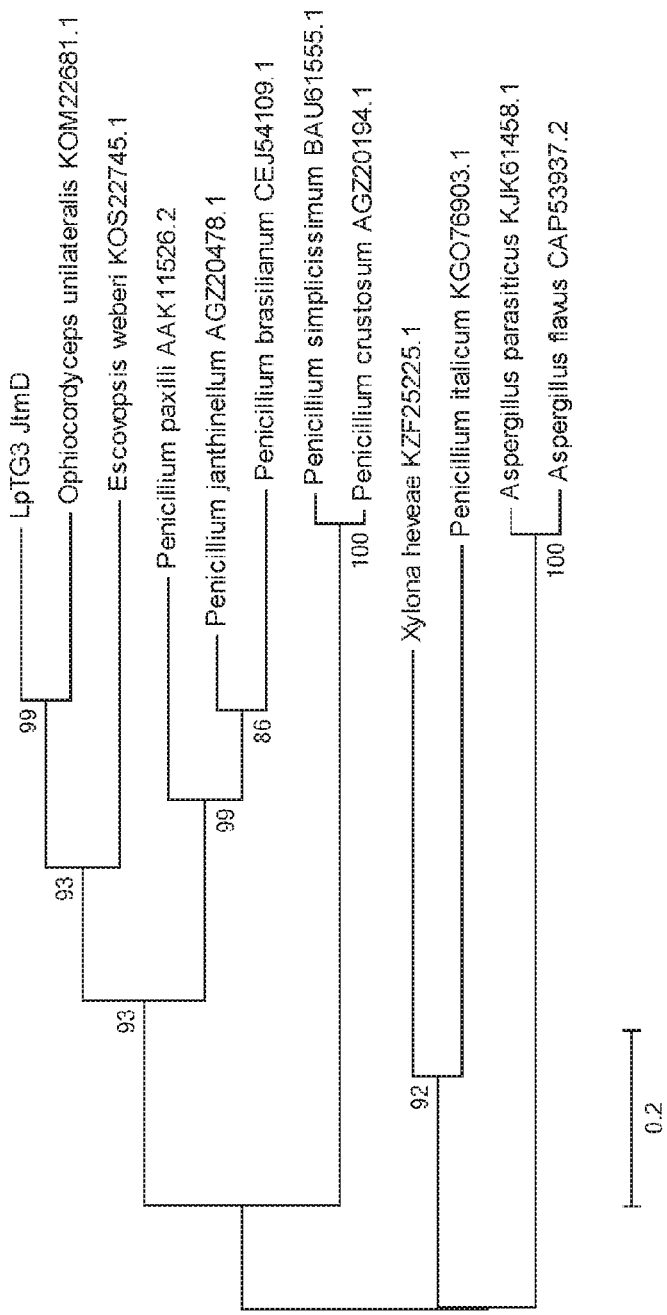

FIG. 15. Bootstrap consensus tree generated through Maximum Likelihood analysis of the predicted amino acid sequence of JtmD from LpTG-3 (NEA12) and the top 11 BLASTp hits in the NCBI database. Multiple alignment of complete predicted protein sequences was performed using ClustalW with default parameters. To construct tree topology, maximum likelihood (ML) was used as implemented in MEGA 6 with default parameters and 500 bootstrap replicates. Branches with bootstrap values of greater than 70% from 500 bootstrap replication are marked next to each branch. Genbank accession numbers for each protein sequence is provided in each tree diagram. JtmD exhibits amino acid sequence identity to aromatic prenyl transferases: KOM22681.1 [67%; *O. unilateralis*]; AGZ20478.1 [49%; *P. janthinellum*]; AAK11526.2 [46%; *P. paxilli*]; KOS22745.1 [50%; *E. webers*]; CEJ54109.1 [47%; *P. brasilianum*]; BAU61555.1 [31%; *P. simplicissimum*]; AGZ20194.1 [31%; *P. crustosum*]; KZF25225.1 [33%; *Xylona heveae* TC161]; KGO76903.1 [30%; *P. italicum*]; KJK61458.1 [31%; *Aspergillus parasiticus* SU-1]; CAP53937.2[[31%; *Aspergillus flavus*].

Figure 16:
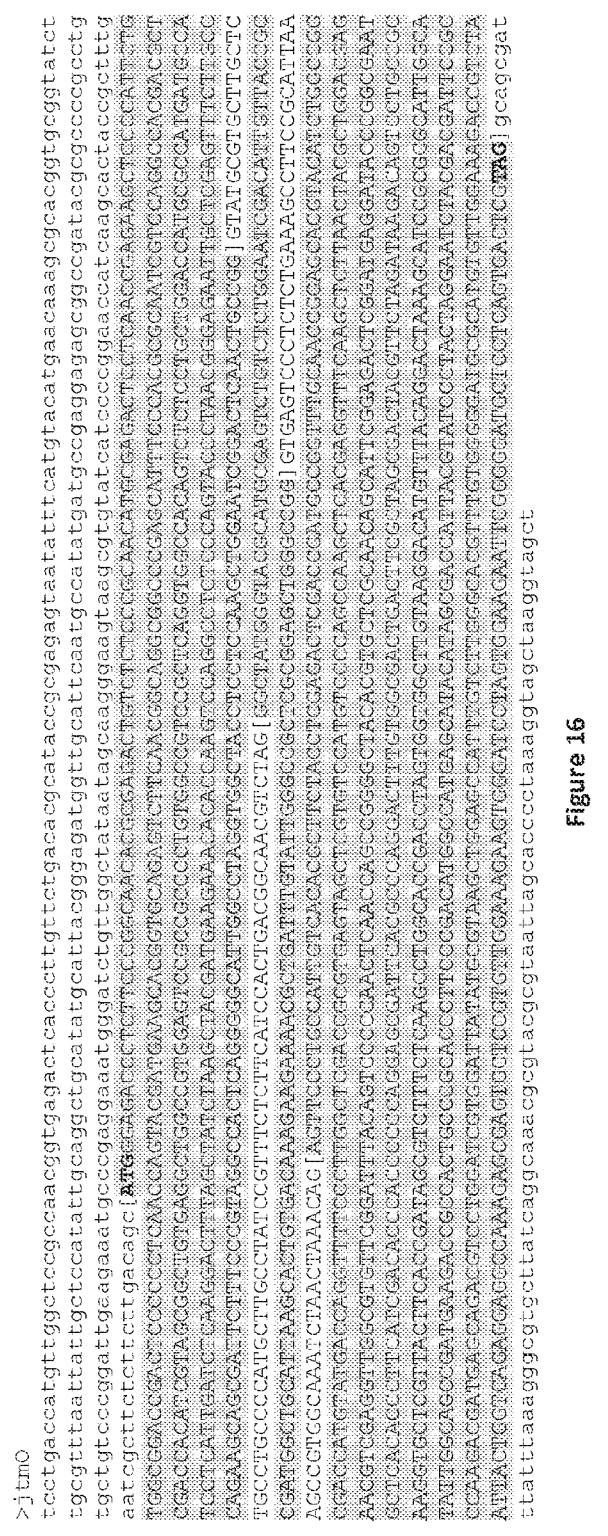

FIG. 16. Nucleotide sequence for the jtmO gene (Sequence ID No 13). The coding sequence for the predicted JtmO protein is highlighted in grey (Sequence ID No 14). Start (ATG) and stop (TAG) codon sequences are shown in bold. Untranslated 5' and 3' sequences are shown in lowercase. The complete nucleotide sequence for the jtmO gene was identified by mapping RNA reads from the in planta (Alto-NEA12) transcriptome data described in FIG. 6 followed by extraction of the DNA sequence from NEA12 PacBio contig 3.

FIG. 17. JtmO is predicted to be a FAD-binding oxidoreductase 479 amino acids in length (Sequence ID No 15). JtmO exhibits highest homology to a predicted protein (6-hydroxy-D-nicotine oxidase) from Escovopsis weberi (KOS22754.1) (Sequence ID No 16). Protein identity: 271/481 (56.3%); Protein similarity: 344/481 (71.5%); Gaps: 39/481 (8.1%). Sequences were aligned using EMBOSS Needle.

Figure 18:
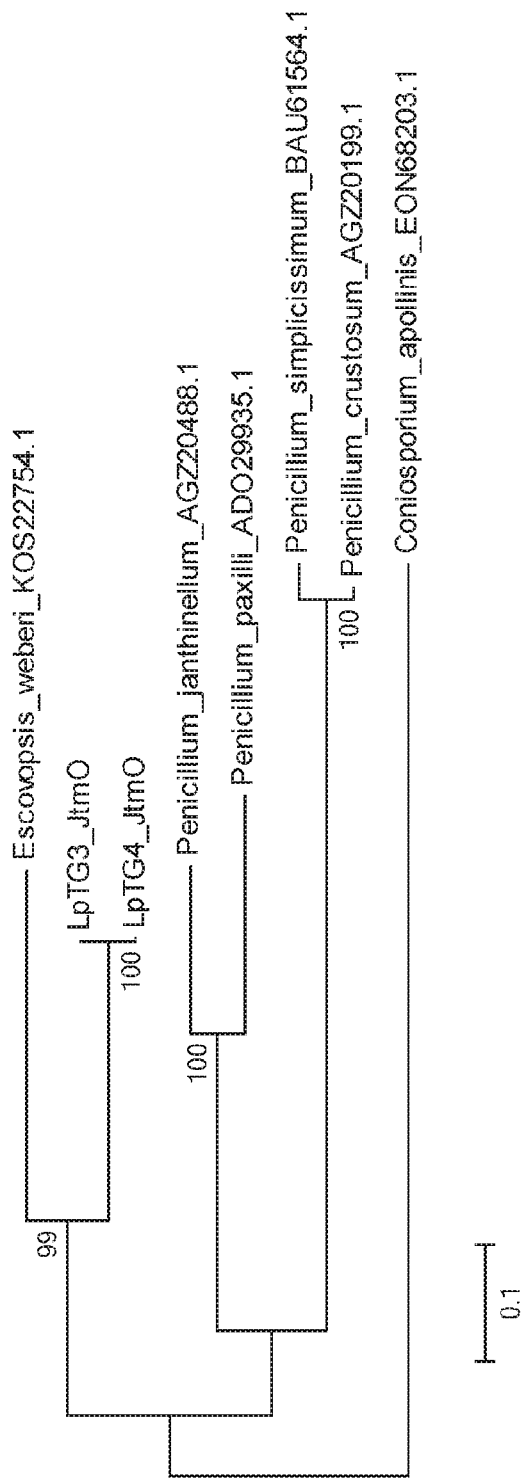

FIG. 18. Bootstrap consensus tree generated through Maximum Likelihood analysis of the predicted amino acid sequence of JtmO from LpTG-3 (NEA12) and LpTG-4 (E1) and the top 6 BLASTp hits in the NCBI database. Multiple alignment of complete predicted protein sequences was performed using ClustalW with default parameters. To construct tree topology, maximum likelihood (ML) was used as implemented in MEGA 6 with default parameters and 500 bootstrap replicates. Branches with bootstrap values of greater than 70% from 500 bootstrap replication are marked next to each branch. Genbank accession numbers for each protein sequence is provided in each tree diagram. JtmO exhibits amino acid sequence similarity to FAD-binding oxidoreductases: KOS22754.1 [56%; Escovopsis webers]; AGZ20488.1 [52%; P. janthinellum]; ADO29935.1 [49%; P. paxilli]; BAU61564.1 [43%; P. simplicissimum]; AGZ20199.1 [43%; P. crustosum]; EON68203.1 [Coniosporium apollinis].

Figure 19A:
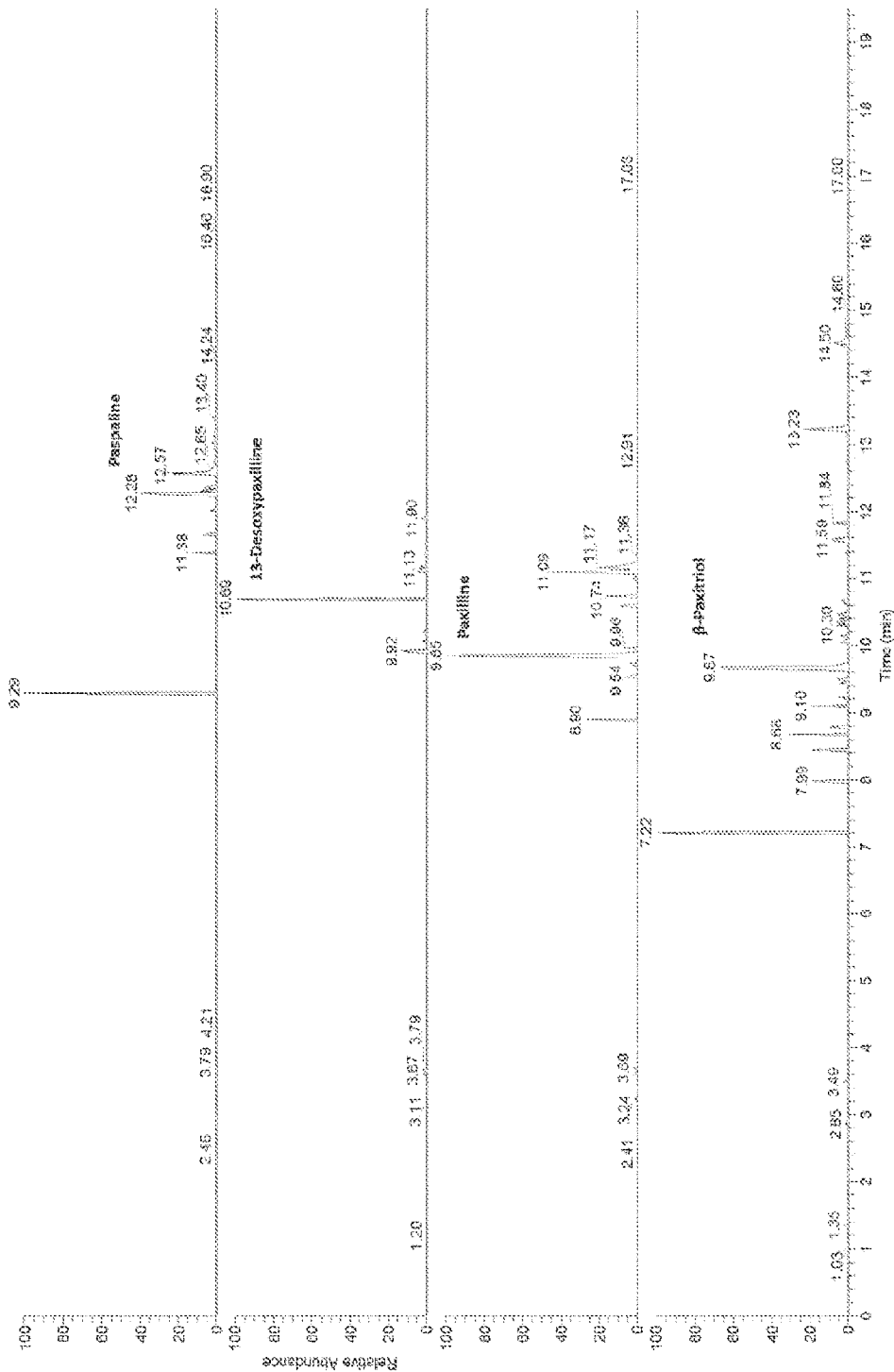
Figure 19B:
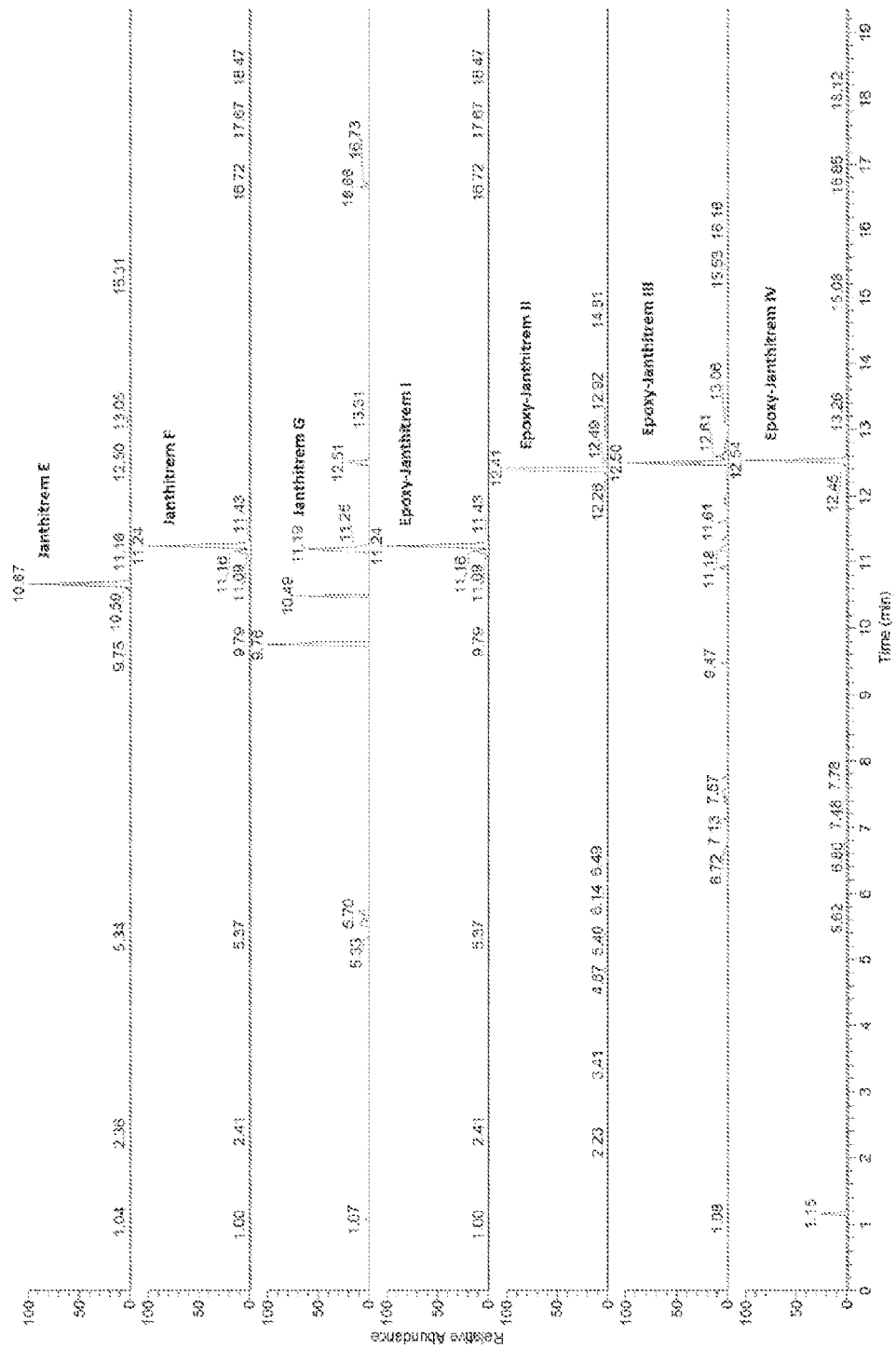

FIG. 19. LC-ESI-FTMS extracted ion chromatogram of metabolites observed in perennial ryegrass- LpTG-3 associations, collected from 0-20 min in positive ionisation mode (ESI+).

Figure 20:
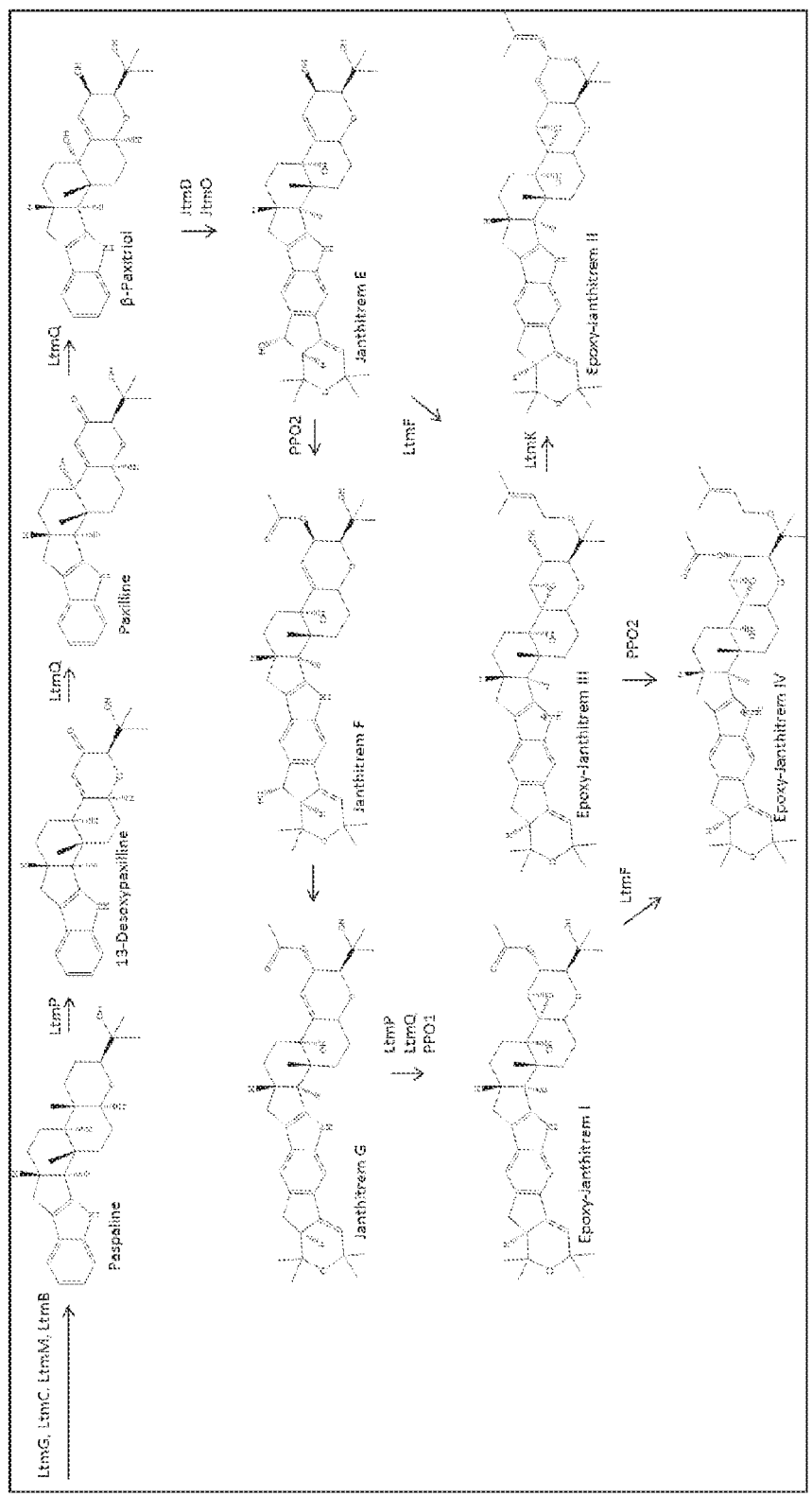

FIG. 20. Proposed pathway for epoxy-janthitrem biosynthesis. The suggested scheme follows the indole-diterpene biosynthetic pathway, illustrating a parsimonious route to epoxy-janthitrem I (11, 12-epoxjanthitrem G) and its variants (epoxy-janthitrems II-IV). All metabolites were observed by LC-MS/MS (FIG. 19).

FIG. 21. Nucleotide sequence of jtmD (Sequence ID No 17). Gene sequences selected for generation of RNAi silencing vectors are highlighted: Gene sequences selected for cassette 2, 3 and 4 are shown in italics (Sequence ID No 18)., underlined (Sequence ID No 19). and in bold respectively (Sequence ID No 20).

FIG. 22. Schematic diagram of gene silencing vectors. To generate the entry clones, gene cassettes [inverted repeats of candidate gene sequences, separated by a 147 bp spacer (cutinase gene intron from M. grisea) and containing attB1 and attB2 sites], were cloned into the pDONR 221 vector using BP clonase (Invitrogen, USA). The Gateway™-enabled destination vector (pEND0002) was constructed through modifications of the T-DNA region of pPZP200 containing hph gene (selectable marker) under the control of trpCP (Aspergillus nidulans tryptophan biosynthesis promoter) and trpCT (A. nidulans tryptophan biosynthesis terminator and first reading frame A [RFA-A] cassette (gateway) under the control of gpdP (A. nidulans glyceraldehyde-3-phosphate dehydrogenase promoter) and trpCT (A. nidulans tryptophan biosynthesis terminator). The final RNA silencing vectors were produced by LR clonase reaction between an entry vector and the pEND002 vector.

Figure 23:
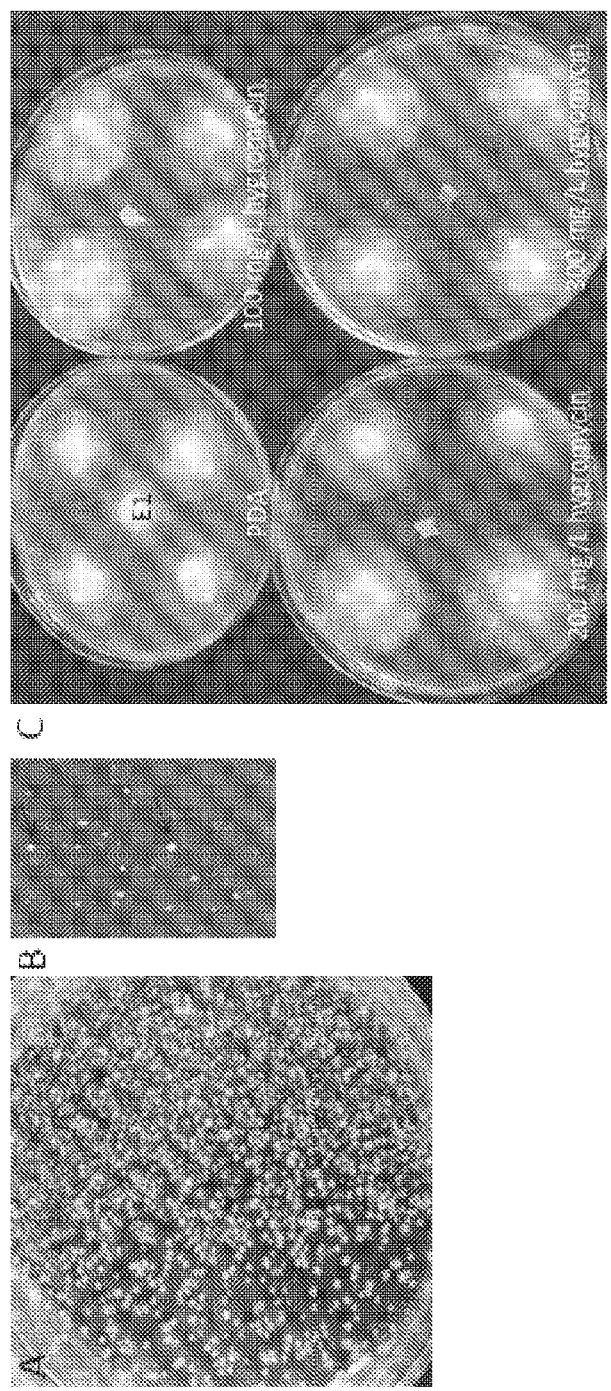

FIG. 23. Fungal protoplast regeneration. A. Regeneration of fungal protoplasts without hygromycin selection, assessment of protoplast viability. B. Regeneration of fungal protoplasts transformed with RNA silencing vector on hygromycin selection (arrows indicate individual colonies). C. Recovery of E1 strains carrying an RNA silencing vector on hygromycin selection.

DETAILED DESCRIPTION OF THE PREFERRED EMBODIMENTS

Identification of Genes for Janthitrem Biosynthesis in LpTG-3 Endophyte Strain NEA12

Whole genome sequence analysis was used to identify candidate genes for janthitrem biosynthesis in the NEA12 genome. The protein sequences LtmE and LtmJ from Standard Endophyte (SE) strain were used as query sequences to search the predicted protein database derived from the NEA12 genome. Using this approach, BLASTp searches yielded 13 putative LtmE protein homologues and 26 putative LtmJ protein homologues in the library of predicted NEA12 proteins.

The NEA12 genome is expected to have predicted LtmE and ltmJ protein homologues in common with the SE strain. However, candidates for janthitrem production would be unique to LpTG-3 and LpTG-4 genomes. As SE does not produce janthitrems, further analysis was performed to reduce the number of candidates to those present only in LpTG-3 and LpTG-4 endophytes. Each of the 13 putative LtmE protein homologues and 26 putative LtmJ protein homologues were used as a BLASTx query of the predicted SE protein database. A single ltmE NEA12 homologue (g30.t1) was identified in this analysis (Table 1) and therefore the best likely candidate for further investigation. The predicted protein sequence for gene g30.t1 has homology to aromatic prenyl transferases from P. janthinellum (JanD; 49%) and P. paxilli (PaxD; 46%) (Table 2). These genes are associated with synthesis of the indole diterpenes shearinine K and paxilline respectively. The gene g30.t1 is therefore henceforth referred to jtmD.

TABLE 1

BLASTx analysis of putative LtmE and LtmJ protein homologues from NEA12 to the SE predicted protein database identified g30.t1 as the most likely candidate gene for janthitrem biosynthesis in NEA12.

| query id | subject id | % identity | alignment length | mismatches | gap opens | q. start | q. end | s. start | s. end | evalue | bit score |
|---|---|---|---|---|---|---|---|---|---|---|---|
| g2.t1 | g1806.t1 | 99.75 | 403 | 1 | 1 | 1 | 403 | 1 | 403 | 0 | 838 |
| g30.t1 | g4103.t1 | 28.05 | 385 | 256 | 12 | 22 | 395 | 10 | 384 | 1.00e−37 | 152 |
| g5701.t1 | g6522.t1 | 86.85 | 502 | 25 | 3 | 1 | 483 | 1 | 480 | 0 | 796 |
| g98.t1 | g1890.t1 | 99.4 | 332 | 1 | 1 | 1 | 331 | 1 | 332 | 0 | 678 |

TABLE 1-continued

BLASTx analysis of putative LtmE and LtmJ protein homologues from NEA12 to the SE predicted protein database identified g30.t1 as the most likely candidate gene for janthitrem biosynthesis in NEA12.

| query id | subject id | % identity | alignment length | mis-matches | gap opens | q. start | q. end | s. start | s. end | evalue | bit score |
|---|---|---|---|---|---|---|---|---|---|---|---|
| g7273.t1 | g1977.t1 | 89.06 | 466 | 14 | 3 | 1 | 440 | 1 | 455 | 0 | 827 |
| g6270.t1 | g7010.t1 | 99.63 | 537 | 2 | 0 | 1 | 537 | 1 | 537 | 0 | 1097 |

Identification of the Janthitrem Biosynthetic Gene Cluster in the LpTG-3 Genome

The NEA12 genome was sequenced using the PacBio Sequel sequencing platform (PacBio). The contig containing the putative LpTG-3 janthitrem biosynthetic gene cluster was identified using the jtmD gene sequence as a query. The gene content of NEA12 PacBio contig 3 (247 475 kb), containing jtmD, was then annotated using a combination of both Augustus (Stanke and Morgenstern, 2005) gene prediction and manual annotation using the known gene sequences of LTM genes (Young et al., 2005, 2006) and jtmD (Table 2).

NEA12 PacBio contig 3 contains 13 predicted and known genes (FIG. 4). Cluster 1 (ItmG, ItmS, ItmM, ItmK) and Cluster 2 (ItmP, ItmQ, ItmF, ItmC, ItmB) are located at c. 57243-67332 bp and c. 6838-16951 bp respectively (Table 2). The order and orientation of genes within Cluster 1 and Cluster 2 is maintained as compared to the *Epichloë festucae* var. *lolli* and *Epichloë festucae* LTM loci (Young et al., 2006; Saikia et al., 2008). Downstream of ItmK, a polyketide synthase (pks) pseudogene (also described by Young et al., 2005), containing several frame-shift mutations, flanked on the right by an additional AT-rich sequence was observed. The topology of the partial LpTG-3 (NEA12) LTM locus is more similar to that of the *Epichloë festucae* (FI1) LTM locus than the *Epichloë festucae* var. *lolii* (Lp19) which has two retrotransposon relics inserted between ItmK and the pks pseudogene (Saikia et al., 2008).

The pks pseudogene defines the left-hand boundary between sequence in common to LpTG-3 and *Epichloë festucae* var. *lolli* (PacBio contig 3: 1 bp-c.70039 bp) and a previously undescribed genome sequence unique to janthitrem producing strains from the taxa LpTG-3 and LpTG-4 (PacBio contig 3: c.70039 bp-247475 bp) (FIG. 4). The right hand boundary to this region is defined by the end of PacBio contig 3 (247475 bp). This region of the NEA12 genome is characterised by 4 genes, a transposase with a MULE domain (159248 bp-163900 bp), a Helitron helicase-like transposable element (170950 bp-175054 bp), and three AT-rich regions (FIG. 5). Two novel gene clusters termed Cluster 3 and Cluster 4, each containing 2 genes, were identified on NEA12 PacBio contig 3 (Table 2; FIG. 4).

The genomes of representative strains of *Epichloë* sp. endophytes from 4 taxa—*Epichloë festucae* var. *lolii* (SE, NEA2, NEA6, NEA10), LpTG-2 (NEA11), LpTG-3 (NEA12, AR37, 15310, 15311), LpTG-4 (E1) and FaTG-3 (NEA23)—were mapped to NEA12 PacBio contig 3. A region unique to janthitrem producing taxa LpTG-3 and LpTG-4 was identified (PacBio contig 3: c.70039 bp-247475 bp) while for endophytes from *Epichloë festucae* var. *lolii*, LpTG-2 and FaTG-3 this region was absent (FIG. 5). None of the genes in this region had been previously described in *Epichloë* endophytes.

TABLE 2

Sequence analysis of genes and other features identified in NEA12 PacBio contig 3.

| | Position in NEA12 PacBio contig 3 (bp) | | | | Top BLASTp Hit | | | |
|---|---|---|---|---|---|---|---|---|
| Gene ID | start | end | Gene cluster | Predicted function | Homologous gene | Percent Identity (aa) | Organism | Genbank Accession No. | Reference |
| ItmP | 6838 | 7843 | 2 | Cytochrome P450 monooxygenase | ItmP | 100% | Epichloë festucae var. lolii | DQ443465 | Young et al, 2006 |
| ItmQ | 9169 | 11557 | 2 | Cytochrome P450 monooxygenase | ItmQ | 100% | Epichloë festucae var. lolii | DQ443465 | Young et al, 2006 |
| ItmF | 12830 | 14082 | 2 | Prenyl transferase | ItmF | 99% | Epichloë festucae var. lolii | DQ443465 | Young et al, 2006 |
| ItmC | 16001 | 14888 | 2 | Prenyl transferase | ItmC | 100% | Epichloë festucae var. lolii | DQ443465 | Young et al, 2006 |
| ItmB | 16370 | 16951 | 2 | Integral membrane protein | ItmB | 100% | Epichloë festucae var. lolii | DQ443465 | Young et al, 2006 |
| ItmG | 57243 | 58343 | 1 | GGPP synthase | ItmG | 99% | Epichloë festucae var. lolii | AY742903 | Young at al., 2005 |
| ItmS | 59651 | 60554 | 1 | Integral membrane protein | ItmS | 100% | Epichloë festucae var. lolii | AY742903 | Young et al., 2005 |
| ItmM | 61702 | 63348 | 1 | FAD-dependent monooxygenase | ItmM | 99% | Epichloë festucae var. lolii | AY742903 | Young at al., 2005 |
| ItmK | 65270 | 67332 | 1 | Cytochrome P450 monooxygenase | ItmK | 99% | Epichloë festucae var. lolii | AY742903 | Young at al., 2005 |
| ψpks | 68047 | 69091 | — | Polyketide synthase (pseudogene) | | 73% | Fusarium equiseti | ALQ32965.1 | unpublished |
| PP01 | 117514 | 116031 | 3 | Cytochrome P450 monooxygenase | hypothetical protein | 68% | Hirsutella minnesotensis | KJZ77225 | Lai et al., 2014 |

TABLE 2-continued

Sequence analysis of genes and other features identified in NEA12 PacBio contig 3.

| Gene ID | Position in NEA12 PacBio contig 3 (bp) | | Gene cluster | Predicted function | Top BLASTp Hit | | | | |
|---|---|---|---|---|---|---|---|---|---|
| | start | end | | | Homologous gene | Percent Identity (aa) | Organism | Genbank Accession No. | Reference |
| PP02 | 118533 | 119536 | 3 | Membrane bound O-acyl transferase | hypothetical protein | 34% | Oidiodendron maius Zn | KIM95229 | unpublished |
| jtmD | 150720 | 151982 | 4 | Aromatic prenyl transferase | hypothetical protein | 68% | Ophiocordyceps unilateralis | KOM22681 | de Bekker et al., 2015 |
| PP03 | 159248 | 163900 | 4 | Transposase | hypothetical protein | 86% | Hirsutella minnesotensis | KJZ68513 | Lai et al., 2014 |
| jtmO | 164992 | 166560 | 4 | 6-hydroxy-D-nicotine oxidase | hypothetical protein | 59% | Escovopsis weberi | KOS22754 | unpublished |
| TE | 170950 | 175054 | — | Transposable element | | 85% | Hirsutella minnesotensis | KJZ70955 | Lai et al., 2014 |

Transcript Expression of Genes Located Within PacBio Contig 3

In planta expression of candidate genes for janthitrem biosynthesis in LpTG-3 (NEA12), LpTG-4 (E1) and *Epichloë festucae* var. *lolii* (SE) was determined using RNA-seq analysis of perennial ryegrass-endophyte association transcriptome data by mapping the reads generated from two perennial ryegrass-endophyte transcriptome studies to NEA12 PacBio contig 3 (FIG. 6). In study one, transcriptome analysis was performed to study the major changes that occur in host and endophyte transcriptomes during seedling growth and maturation at six timepoints, from post imbibition (0 hours) to 10 day old seedlings (10 days) (Sawbridge, 2016). Transcript expression for genes within NEA12 PacBio contig 3 in perennial ryegrass cultivar Alto-SE and Alto-NEA12 at two time points (0 hours and 10 days) is shown here. In study two, a transcriptome atlas derived from distinct tissue types of perennial ryegrass-endophyte association Impact-E1 was developed (Cogan et al., 2012). Transcript expression for genes within NEA12 PacBio contig 3 in two tissue types, leaf and stigma are shown here.

In addition to the previously defined Cluster 1 and Cluster 2 genes, the genes proposed to be involved in janthitrem biosynthesis, PP01, PP02, jtmD and jtmO are also expressed. As Cluster 3 and Cluster 4 genes are not present in the *Epichloë festucae* var. *lolii* (SE) genome, expression of these genes was not observed by SE in planta.

Detailed Description of the Four Gene Clusters on NEA12 PacBio Contig 3

Cluster 1 (LTM1) and Cluster 2 (LTM2)

Core genes for the initial stages of indole-diterpene biosynthesis in *Epichloë* spp. are present in LpTG-3 endophyte NEA12. Genes ItmG, ItmC and /trnM are predicted to encode a generanyl geranyl diphosphate synthase, a prenyl transferase and a FAD-dependent monooxygenase with 99%, 100%, 99% amino acid sequence identity compared with their respective Ltm homologues in *Epichloë festucae* var. *lolii*. The predicted protein product of ItmB (100%), an integral membrane protein, together with ItmM are proposed to catalyse epoxidation and cyclisation of the diterpene skeleton for paspaline biosynthesis. Genes ItmP (100%) and ItmQ (100%) encode cytochrome P450 monooxygenases and complete the collection of 6 genes required for paxilline biosynthesis in *Epichloë* spp.

Cluster 3 Genes

Cluster 3 (116033 bp-119536 bp) contains 2 genes, predicted gene PP01 (predicted protein 1), a putative cytochrome P450 monoxygenase, and PP02, predicted to be a membrane bound O-acyl transferase (MBOAT) protein (Table 2).

PP01

The nucleotide sequence for the PP01 gene is shown in FIG. 7. PP01 shows homology to a putative cytochrome P450 monoxygenase from *Hirsutella minnesotensis* (FIG. 8; KJZ77225.1), an endoparasitic fungi of the soybean cyst nematode (Heterodera glycines). PP01 may have a role in janthitrem biosynthesis, however, PP01 does not have a homolog in any other indole-diterpene gene cluster characterized to date. For example, PP01 does not share sequence similarity with previously described cytochrome P450 monoxygenases (e.g. LtmP, LtmQ/PaxQ/AtmQ, LtmK) involved in indole-diterpene biosynthesis (FIG. 9). The predicted protein sequence of PP01 from E1 (LpTG-4) has 1 amino acid difference (at amino acid 42 D>G) to that of NEA12 (LpTG-3).

PP02

The nucleotide sequence for the PP02 gene is shown in FIG. 10. PP02 is predicted to be a membrane bound O-acyl transferase (MBOAT) protein (FIG. 11; FIG. 12). The predicted protein sequence of PP02 from E1 (LpTG-4) is identical that of NEA12 (LpTG-3). While membrane associated, PP02 is not a transmembrane protein based on prediction analysis with TMHMM.

Cluster 4

Cluster 4 (150720 bp-175051 bp) contains 2 genes, JtmD an aromatic prenyl transferase, and JtmO predicted to encode a FAD-binding oxidoreductase.

JtmD

The nucleotide sequence for the jtmD gene is shown in FIG. 13. JtmD, predicted to be an aromatic prenyl transferase, exhibits highest homology to a predicted protein from *Ophiocordyceps unilateralis* (63%; FIG. 14). The predicted protein sequence for JtmD also has homology to aromatic prenyl transferases such as those from *P. janthinellum* (JanD; 49%) and *P. paxilli* (PaxD; 46%) (FIG. 15; Nicholson et al., 2015). These genes are associated with synthesis of the indole diterpenes shearinine K and paxilline respectively. The predicted protein sequence of JtmD from NEA12 (LpTG-3) is identical that of E1 (LpTG-4).

JtmO

The nucleotide sequence for the jtmO gene is shown in FIG. 16. JtmO exhibits highest homology to a predicted protein (6-hydroxy-D-nicotine oxidase) from *Escovopsis weberi* (59%; FIG. 17). JtmO also has homology to JanO, predicted to be a FAD-binding oxidoreductase, associated with synthesis of shearinines in *P. janthinellum* (52%; Nicholson et al., 2015). Genes with similar predicted functions have been identified other indole-diterpene gene clusters (FIG. 18). The JtmO protein product is likely to have a role in the subsequent modification of the indole-diterpene core. The predicted protein sequence of JtmO in NEA12 (LpTG-3) and E1 (LpTG-4) is 97.9% identical. The E1 JtmO predicted protein has a 9 amino acid deletion (aa 12-20) and one amino acid change (T>A at amino acid 326) compared to that of NEA12.

JtmO

The nucleotide sequence for the jtmO gene is shown in FIG. 16. JtmO exhibits highest homology to a predicted protein (6-hydroxy-D-nicotine oxidase) from *Escovopsis weberi* (59%; FIG. 17). JtmO also has homology to JanO, predicted to be a FAD-binding oxidoreductase, associated with synthesis of shearinines in *P. janthinellum* (52%; Nicholson et al., 2015). Genes with similar predicted functions have been identified other indole-diterpene gene clusters (FIG. 18). The JtmO protein product is likely to have a role in the subsequent modification of the indole-diterpene core. The predicted protein sequence of JtmO in NEA12 (LpTG-3) and E1 (LpTG-4) is 97.9% identical. The E1 JtmO predicted protein has a 9 amino acid deletion (aa 12-20) and one amino acid change (T>A at amino acid 326) compared to that of NEA12.

All of the indole-diterpene gene clusters identified to date have a core set of genes for the synthesis of paspaline, and a suite of additional genes that encode multi-functional cytochrome P450 monooxygenases, FAD dependent monooxygenases and prenyl transferases that catalyse various regio- and stereo-specific oxidations on the molecular skeleton to generate a diversity of indole-diterpene products.

Robust liquid chromatography-mass-spectrometry (LC-MS) approaches were employed to targeted key metabolites associated with the biosynthesis of indole-diterpene alkaloids.

The extracted ion chromatograms of these metabolites, isolated in planta from perennial ryegrass-LpTG-3 associations are illustrated in FIG. 19. The observed accurate masses and fragmentation patterns (via LC-MS/MS analysis) are indicated in Table 3.

While applicant does not wish to be restricted by theory, based on the identification and fragmentation of these metabolites, we have proposed a framework for the biosynthesis of the epoxy-janthitrems (FIG. 20). Here, we propose that janthitrem biosynthesis is likely to arise from the synthesis of paspaline to p-paxitriol by LtmP and LtmQ. JtmD and JtmO are required for the initial biosynthesis of janthitrems, followed by PP01 and PP02. LtmF and LtmK are required for the synthesis of the epoxy-janthitrems II and IV.

TABLE 3

Targeted LC-MS/MS analysis of the proposed metabolites associated with the biosynthesis of epoxy-Janthitrem I and its derivatives (epoxy-Janthitrem II-IV), following the indole-diterpene alkaloid biosynthetic pathway for LpTG-3 endophytes in planta. To identify each metabolite, accurate masses (m/z), retention times (RT) and MSn fragmentation data (LC-MS/MS) were acquired in positive ionisation mode [M + H] using a Thermo Fisher Q-Exactive Plus orbitrap mass spectrometer. Accurate mass and MSn fragmentation results were compared with theoretical masses and fell within the range of 5 ppm difference (Delta ppm).

| Metabolite | m/z [M + H] | RT (min) | Production: LC-MS/MS 1 | 2 | 3 | 4 | Chemical Formula [M + H] | Theoretical Mass [M + H] | Delta (ppm) |
|---|---|---|---|---|---|---|---|---|---|
| Paspaline | 422.3034 | 12.28 | 130.0651 | 182.0960 | 407.2766 | | C28 H40 O2 N | 422.3054 | −4.7 |
| 13-Desoxypaxilline | 420.2534 | 10.69 | 130.0651 | 182.0963 | 402.2420 | | C27 H34 O3 N | 420.2533 | 0.09 |
| Paxilline | 436.2482 | 9.85 | 130.0650 | 182.0961 | 346.1795 | | C27 H34 O4 N | 436.2482 | −0.15 |
| β-Paxitriol | 436.2482 | 9.67 | 130.0651 | 182.0960 | 335.2132 | | C27 H36 O4 N | 438.2639 | 2.36 |
| Janthitrem E | 604.3637 | 10.60 | 222.1276 | 280.1694 | 546.3211 | 589.3346 | C37 H50 O6 N | 604.3633 | 0.7 |
| Janthitrem F | 646.3735 | 11.24 | 222.1277 | 280.1696 | 588.3320 | 631.3459 | C39 H52 O7 N | 646.3738 | −0.5 |
| Janthitrem G | 630.3807 | 11.19 | 222.1274 | 392.1917 | | 615.3461 | C39 H52 O6 N | 630.3789 | 2.9 |
| Epoxy-janthitrem I | 646.3735 | 11.24 | 222.1277 | 280.1696 | 588.3320 | 631.3459 | C39 H52 O7 N | 646.3738 | −0.5 |
| Epoxy-janthitrem II | 670.4076 | 12.41 | 222.1275 | 280.1692 | 612.3676 | 655.3814 | C42 H56 O6 N | 670.4102 | −3.8 |
| Epoxy-janthitrem III | 672.423 | 12.50 | 222.1274 | 280.1692 | 614.3833 | 657.3969 | C42 H58 O6 N | 672.4259 | −4.3 |
| Epoxy-janthitrem IV | 714.4341 | 12.52 | 222.1278 | 280.1694 | 656.3934 | 699.4081 | C44 H60 O7 N | 714.4364 | −3.3 |

JtmD and JtmO have not previously been described in *Epichloë* endophytes. Homologues of the two genes have been identified in a number of *Penicillium* species (e.g. *P. janthinellum, P. paxilli, P. crustosum*) and are often found located side by side. It is interesting to note that in the *Escovopsis weberi* genome (GenBank: LGSR01000002.1), the two gene homologues identified in this study (JtmD: KOS22745.1; JtmO: KOS22754.1) are also found to be adjacent to each other. *Escovopsis* sp. are parasitic microfungi that rely on other fungi to be their hosts.

Proposed Biosynthetic Pathway for Janthitrem Production

The work described here provides a genetic basis for janthitrem biosynthesis in *Epichloë* endophytes, specifically LpTG-3 and LpTG-4. While applicant does not wish to be restricted by theory, it is likely that in addition to these two asexual taxa there is (or once was) at least one ancestral sexual *Epichloë* species that synthesises janthitrems.

Functional Analysis of Candidate Genes Required for Epoxy-Janthitrem I Biosynthesis RNAi Silencing of the jtmD Gene Vector Construction Three candidate gene sequences (95 bp, 129 bp and 432 bp) within jtmD were selected for design of RNAi silencing vectors (FIG. 21). To generate the entry clones, gene cassettes were cloned into the pDONR 221 vector. RNA silencing vectors (FIG. 22) were produced by LR clonase reaction between an entry clones and the Gateway™-enabled destination vector (pEND0002) (Hettiarachchige, 2014).

Isolation of Fungal Protoplasts

Mycelia were harvested, under sterile conditions, by filtration through layers of miracloth lining a funnel and washed 3 times with 30 mL of sterile ddH$_2$O. Mycelia were washed with 10 mL of OM buffer (1.2M MgSO$_4$.7H$_2$O, 10 mM Na$_2$HPO$_4$, 100 mM NaH$_2$PO$_4$.2H$_2$O, pH 5.8) and transferred to a sterile 250 mL plastic vessel. Freshly prepared 10 mg/mL Glucanex (30 mL) (Sigma Aldrich) in OM was added and incubated for 18 hrs at 30° C. with gentle shaking (80-100 rpm). The glucanex/protoplast solution (30-50 µL) was examined under a microscope to confirm successful digestion. Protoplasts were filtered through miracloth in a funnel, into 15 mL sterile glass centrifuge tubes (Gentaur, Belgium) and placed on ice. Each tube was carefully overlaid with 2 mL of ST buffer (0.6 M sorbitol, 100 mM Tris-HCl, pH 8.0) and centrifuged (Beckman coulter, Avanti® J-251) (5000 rpm for 5 min at 4° C.). Following centrifugation, protoplasts formed a white layer between the glucanex solution and ST buffer and this layer was carefully removed. STC buffer (1 M sorbitol, 50 mM CaCl$_2$.2H$_2$O, 50 mM Tris-HCl, pH 8.0) (5 mL) was added to the protoplast solution in fresh sterile glass tubes. Samples were gently inverted once and centrifuged (5000 rpm for 5 min at 4° C.). Protoplast pellets were pooled with 5 mL of STC buffer and centrifugation was repeated (5000 rpm for 5 min at 4° C.) until only one pellet remained. Excess STC buffer was removed, and the final protoplast pellet was re-suspended in 500 µL of STC buffer. Protoplast concentration was estimated by diluting protoplasts (1/100 and/or 1/1000 with STC buffer) and counting using a Haemocytometer and microscope. Protoplasts were diluted with STC to 1.25×10$^8$ protoplasts/mL.

PEG-Mediated Fungal Protoplast Transformation

Prior to delivery into fungal protoplasts, the three RNA silencing vectors (FIG. 22) were verified by restriction enzyme digestion and Sanger sequencing (data not shown). High quality plasmid DNA, suitable for transformation into fungal protoplasts was produced, using PureYield™ Plasmid Midiprep System (Promega), according to manufacturers' instructions. Aliquots (80 µL) of diluted protoplasts (1.25×10$^8$ protoplasts/mL) were prepared on ice. To each aliquot, added; 2 µL 50 mM spermidine, 5 µL 5 mg/mL heparin (prepared in STC buffer), 10 µg plasmid DNA (1 µg/µL, not exceeding 20 µL) and 20 µL 70% (w/v) PEG solution [70% (w/v) PEG 4000, 10 mM Tris-HCl pH 8.0, 10 mM CaCl$_2$]. Eppendorf tubes were gently mixed and incubated on ice for 30 min. Following the addition of 1.5 mL STC buffer, protoplasts were mixed and centrifuged (Eppendorf, Centrifuge 5424 R) (5000 rpm for 5 min at 4° C.). The supernatant was removed and protoplasts were resuspended in regeneration medium II (RG II, 500 µL) (304 g/L sucrose, 1 g/L KH$_2$PO$_4$, 1 g/L NH$_4$NO$_3$, 1 g/L NaCl, 0.25 g/L anhydrous MgSO$_4$, 0.13 g/L CaCl$_2$.2H$_2$O, 1 g/L yeast extract, 12 g/L dehydrated potato dextrose, 1 g/L peptone, 1 g/L acid hydrolysate of casein) and incubated overnight (22° C., dark, 45 rpm).

Fungal Protoplast Regeneration

Overnight protoplast solution (200 µL) was incubated with 800 µL 40% (w/v) PEG solution [40% (w/v) PEG 4000, 1M sorbitol, 50 mM Tris-HCl pH 8.0, 50 mM CaCl$_2$], at room temperature for 15 min. Molten (50° C.) 0.4% RG II (5 mL) (304 g/L sucrose, 1 g/L KH$_2$PO$_4$, 1 g/L NH$_4$NO$_3$, 1 g/L NaCl, 0.25 g/L anhydrous MgSO$_4$, 0.13 g/L CaCl$_2$.2H$_2$O, 1 g/L yeast extract, 12 g/L dehydrated potato dextrose broth, 1 g/L peptone, 1 g/L acid hydrolysate of casein, 4 g/L agarose) containing 100 µL of the protoplast/PEG mixture was spread evenly across 0.6% RG II agarose petri dishes (304 g/L sucrose, 1 g/L KH$_2$PO$_4$, 1 g/L NH$_4$NO$_3$, 1 g/L NaCl, 0.25 g/L anhydrous MgSO$_4$, 0.13 g/L CaCl$_2$.2H$_2$O, 1 g/L yeast extract, 12 g/L dehydrated potato dextrose broth, 1 g/L peptone, 1 g/L acid hydrolysate of casein, 6 g/L agarose) containing 100 µg/mL hygromycin B.

Representative RG II petri dishes were retained without hygromycin overlay as controls to assess endophyte viability. All petri dishes were incubated at 22° C. in the dark for 4-6 weeks until regeneration was observed (FIG. 23).

Identification of Transformed Fungal Protoplasts

Individual regenerated colonies were transferred onto petri dishes containing 15% (w/v) potato dextrose agar (PDA) with 100 µg/mL hygromycin selection and incubated (22° C., dark, 10-21 days). Hygromycin resistant colonies were grown in 250 mL sterile culture vessels in PD broth (50 mL) with 100 µg/mL hygromycin (22° C., dark, 150 rpm, 10-21 days) and mycelia were harvested, under sterile conditions, by filtration through layers of miracloth lining a funnel and washed with 30 mL of sterile M9 phosphate buffer (1 g/L NH$_4$Cl, 11 g/L Na$_2$HPO$_4$.7H$_2$O, 3 g/L KH$_2$PO$_4$, 5 g/L NaCl). Washed mycelia was transferred to a Eppendorf tube, lyophilised (24-48 hrs) and DNA extracted using DNeasy Plant Mini Kit (Qiagen, Germany) according to manufacturers' instructions. Transformed individuals were identified by polymerase chain reaction (PCR) for the hygromycin gene (hph; fwd 5'-tgtcgtccatcacagtttgc-3' (Sequence ID NO 21), rev 5'-gcgccgatggtttctacaaa-3' (Sequence ID NO 22), and/or the candidate jtmD gene fragments [jtmD (95 bp) fwd 5'-gccttcttcttgcctgtca-3' (Sequence ID NO 23), rev 5'-gaccgcctgtgtgttttgaa-3' (Sequence ID NO 24); jtmD (129 bp) fwd 5'-cacacagcccaagattgcat-3 (Sequence ID NO 25)', rev 5'-tggaagtctatcgccactgg-3'(Sequence ID NO 26), jtmD (432 bp) fwd 5'-ggagttcagtgcatgctcag-3'(Sequence ID NO 27), rev 5'-ggcaagaagaaaggctcacc-3'(Sequence ID NO 28), carried by the RNA silencing vectors. PCR components and cycling conditions using the CFX Connect™ Real-Time PCR detection system (BioRad) [2xFastStart SYBR Green master mix (Roche), 10 uM forward and reverse primers, 2 µL template DNA, sterile ddH$_2$O (V$_T$ 10 µL); 95° C. 10 min, (95° C. 30 sec, 60° C. 60 sec, 72° C. 30 sec)×40, 60-95° C. (0.5° C. inc.) 5 min]. The assay included appropriate positive and negative control DNA.

Finally, it is to be understood that various alterations, modifications and/or additions may be made without departing from the spirit of the present invention as outlined herein.

REFERENCES

Babu, J. V. (2009) Bioactive chemicals of importance in endophyte-infected grasses. PhD Thesis, University of Waikato, New Zealand.

Cogan, N. O. I., Shinozuka, H., Sawbridge, T. I., Spangenberg, G. C., Forster, J. W. (2012) Development of a transcriptome atlas for perennial ryegrass (*Lolium perenne* L.). In 'Abstracts 7th International Symposium on Molecular Breeding of Forage and Turf'. July 2012, Salt Lake City, Utah, USA. p. 25.

Gallagher, R. T., Latch, G. C., Keogh, R. G. (1980) The janthitrems: fluorescent tremorgenic toxins produced by *Penicillium janthinellum* isolates from ryegrass pastures. *Applied and Environmental Microbiology* 39: 272-273.

Hennessy, L. (2015). Epoxy-janthitrems, effects of temperature on in planta expression and their bioactivity against porina larvae. MSc Thesis. University of Waikato, New Zealand.

Nicholson, M. J., Eaton, C. J., Stärkel, C., Tapper, B. A., Cox, M. P., Scott, B. (2015) Molecular cloning and functional analysis of gene clusters for the biosynthesis of indole-diterpenes in *Penicillium crustosum* and *P. Janthinellum*. Toxins 7 (8): 2701-2722.

Saikia, S., Nicholson, M. J., Young, C., Parker, E. J., Scott, B.(2008) The genetic basis for indole-diterpene chemical diversity in filamentous fungi. Mycological Research 112 (2): 184-199.

Sawbridge, T. I. (2016) Genomic and Transcriptomic Analysis of Perennial Ryegrass/Epichlob Endophytes Symbiota In 'Abstracts Plant and Animal Genome XXIV Conference'. January 2016, San Diego, Calif., USA, W313.

Stanke, M. and Morgenstern, B. (2005) AUGUSTUS: a web server for gene prediction in eukaryotes that allows user-defined constraints. Nucleic Acids Res. 33:465-467.

Young, C. A., Felitti, S., Shields, K., Spangenberg, G., Johnson, R. D., Bryan, G. T., Saikia, S., Scott, B. (2006) A complex gene cluster for indole-diterpene biosynthesis in the grass endophyte Neotyphodium lolii. Fungal Genetic and Biology 43: 679-693.

Young, C. A., Bryant, M. K., Christensen, M. J., Tapper, B. A., Bryan, G. T., Scott, B. (2005) Molecular cloning and genetic analysis of a symbiosis-expressed gene cluster for lolitrem biosynthesis from a mutualistic endophyte of perennial ryegrass. Molecular Genetics and Genomics 274 (1): 13-29.

The invention claimed is:

1. A recombinant nucleic acid construct comprising a heterologous promoter operably linked to a polynucleotide sequence encoding a JtmD protein having aromatic prenyl transferase activity and comprising an amino acid sequence having at least 95% amino acid sequence identity to the amino acid sequence as set forth in SEQ ID NO: 11.

2. A host cell comprising the recombinant nucleic acid construct of claim 1.

3. The recombinant nucleic acid construct of claim 1, wherein said polynucleotide sequence has at least 95% nucleotide sequence identity to the nucleotide sequence as set forth in SEQ ID NO: 10.

4. The recombinant nucleic acid construct of claim 1, wherein said JtmD protein has the amino acid sequence as set forth in SEQ ID NO: 11.

5. The recombinant nucleic acid construct of claim 1, wherein said polynucleotide sequence has the nucleotide sequence as set forth in SEQ ID NO: 10.

* * * * *

SEQUENCE LISTING

<160> NUMBER OF SEQ ID NOS: 28

<210> SEQ ID NO 1
<211> LENGTH: 1484
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 1

```
atgccgtcca ttccgagtct cgcatcgggc ctccaggcat ggctcatcag tggcgtcgtt    60
ctcttgttgg cggcggcggc agtgcttgtc ggacagatgg cggcgtcgcg gccgcgcctt   120
gacgaccgag cgcctcgtct cctgaagggg gcgccgattc tcggctgcct cgacttcttc   180
cgctgccgaa gcgaattcct gctcaagggg agggaccggg accccagccg gcagtttagc   240
ttcttctacg gaccctatcc cattgtcgca ttgtctggct ctgcggcccg gtccttttc    300 tacactgcgc gcggcctcga ctttatccca gggtatatct tcaatttaat gctcgtcaaa   360
acgggccgtg ggcgagctga cacgctgtga aatgctagct ttctggccct cgttgccgca   420
ggcccgagca tcgagcagct cttacccggc ggcgactttc ggaccctctt cgtctcgtct   480
ttcaagcatt tcatgcacaa aaagcagctc gccgccaacc tcggttacct gacgaccgac   540
gcagacgtgg cccttggcgc catcgacaca tcgttgcccg ttgagccctt taagctgatg   600
ctacacctca tctaccagct cagccaccgc gtcctgggga ggcacgacat ttccgacgac   660
cccaagctgc ttgccgacac cgtgtctgcg tttggactcc tcgacgactc gtcggctctc   720
gaggtcatgt tcccccgtgt ccctggccc agcaaggtcc gcaagatgct cgccggtgcc   780
aagttgcacc gcgtgctctc caaaatcacg agcgaccgcc gcaagactcg cagaaccaag   840
agggatgcca tgcagacctt gatggatcaa ggccacccgg atactatcgt gtctgccgta   900
cgccctggtc cccccgtctc ccgctcttat acctcgacac ttataccttg cgtacatgta   960
gctcatcatc ggcgccctca gtgcaggact tgccaatagc gccttcagtg ccgcctggat  1020
ccttgcctac ctttccgtca accgcgagtg gtacgcccgg atacgagccg aagtcgacgc  1080
tgctgttgcc aagcaccgcc gctcgcgggt ggagtcggcg cccgaagtgc tcttgcgcct  1140
gtccatgggc gagtgggagt ccgagttccc aatgatctgc acggccctac gcgagacgat  1200
ccgtatgatt ctgcagctca cgtcaatacg taaaaatatt agcggcaagg atattcagat  1260
tgccgaaact ggcatcatcg cactttgtac ttcgtacaaa aataaattaa atataaatat  1320
gtgaactaat tcaataaatt tctttattga tcggactata tcttgatctt tttaacttaa  1380
ctatttttaa gaattggggg gaaggaaagt tagctactta gtctttcttt cttctttcct  1440
taagtttctt aatactatat taacaccta ttatagctac ctag                    1484
```

<210> SEQ ID NO 2
<211> LENGTH: 1164
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 2

```
atgccgtcca ttccgagtct cgcatcgggc ctccaggcat ggctcatcag tggcgtcgtt      60
ctcttgttgg cggcggcggc agtgcttgtc ggacagatgg cggcgtcgcg ccgcgccctt     120
gacgaccgag cgcctcgtct cctgaagggg gcgccgattc tcggctgcct cgacttcttc     180
cgctgccgaa gcgaattcct gctcaagggg agggaccggg accccagccg cagtttagc     240
ttcttctacg accctatcc cattgtcgca ttgtctggct ctgcggcccg gtccttttc      300
tacactgcgc gcggcctcga ctttatccca ggctttctgg ccctcgttgc cgcaggcccg     360
agcatcgagc agctcttacc cggcggcgac tttcggaccc tcttcgtctc gtctttcaag     420
catttcatgc acaaaaagca gctcgccgcc aacctcggtt acctgacgac cgacgcagac     480
gtggcccttg cgccatcga cacatcgttg cccgttgagc cctttaagct gatgctacac     540
ctcatctacc agctcagcca ccgcgtcctg gggaggcacg acatttccga cgaccccaag     600
ctgcttgccg acaccgtgtc tgcgtttgga ctcctcgacg actcgtcggc tctcgaggtc     660
atgttccccc gtgtcccctg gcccagcaag gtccgcaaga tgctcgccgg tgccaagttg     720
caccgcgtgc tctccaaaat cacgagcgac cgccgcaaga ctcgcagaac caagagggat     780
gccatgcaga ccttgatgga tcaaggccac ccggatacta tcgtgtctgc cctcatcatc     840
ggcgccctca gtgcaggact tgccaatagc gccttcagtg ccgcctggat ccttgcctac     900
ctttccgtca accgcgagtg gtacgcccgg atacgagccg aagtcgacgc tgctgttgcc     960
aagcaccgcc gctcgcgggt ggagtcggcg cccgaagtgc tcttgcgcct gtccatgggc    1020
gagtgggagt ccgagttccc aatgatctgc acggccctac gcgagacgat ccgtatgatt    1080
ctgcagctca cgtcaatacg taaaaatatt agcggcaagg atattcagat tgccgaaact    1140
ggcatcatcg cactttctac ctag                                           1164
```

<210> SEQ ID NO 3
<211> LENGTH: 387
<212> TYPE: PRT
<213> ORGANISM: Unknown
<220> FEATURE:
<223> OTHER INFORMATION: Epichloe sp. Lolium perenne taxonomic group 3
      (LpTG-3)

<400> SEQUENCE: 3

```
Met Pro Ser Ile Pro Ser Leu Ala Ser Gly Leu Gln Ala Trp Leu Ile
1               5                   10                  15

Ser Gly Val Val Leu Leu Ala Ala Ala Val Leu Val Gly Gln
            20                  25                  30

Met Ala Ala Ser Arg Pro Arg Leu Asp Asp Arg Ala Pro Arg Leu Leu
        35                  40                  45

Lys Gly Ala Pro Ile Leu Gly Cys Leu Asp Phe Phe Arg Cys Arg Ser
    50                  55                  60

Glu Phe Leu Leu Lys Gly Arg Asp Arg Asp Pro Ser Arg Gln Phe Ser
65                  70                  75                  80

Phe Phe Tyr Gly Pro Tyr Pro Ile Val Ala Leu Ser Gly Ser Ala Ala
                85                  90                  95
```

```
Arg Ser Phe Phe Tyr Thr Ala Arg Gly Leu Asp Phe Ile Pro Gly Phe
            100                 105                 110

Leu Ala Leu Val Ala Ala Gly Pro Ser Ile Glu Gln Leu Leu Pro Gly
        115                 120                 125

Gly Asp Phe Arg Thr Leu Phe Val Ser Ser Phe Lys His Phe Met His
    130                 135                 140

Lys Lys Gln Leu Ala Ala Asn Leu Gly Tyr Leu Thr Thr Asp Ala Asp
145                 150                 155                 160

Val Ala Leu Gly Ala Ile Asp Thr Ser Leu Pro Val Glu Pro Phe Lys
                165                 170                 175

Leu Met Leu His Leu Ile Tyr Gln Leu Ser His Arg Val Leu Gly Arg
            180                 185                 190

His Asp Ile Ser Asp Asp Pro Lys Leu Leu Ala Asp Thr Val Ser Ala
        195                 200                 205

Phe Gly Leu Leu Asp Asp Ser Ser Ala Leu Glu Val Met Phe Pro Arg
    210                 215                 220

Val Pro Trp Pro Ser Lys Val Arg Lys Met Leu Ala Gly Ala Lys Leu
225                 230                 235                 240

His Arg Val Leu Ser Lys Ile Thr Ser Asp Arg Arg Lys Thr Arg Arg
                245                 250                 255

Thr Lys Arg Asp Ala Met Gln Thr Leu Met Asp Gln Gly His Pro Asp
            260                 265                 270

Thr Ile Val Ser Ala Leu Ile Ile Gly Ala Leu Ser Ala Gly Leu Ala
        275                 280                 285

Asn Ser Ala Phe Ser Ala Ala Trp Ile Leu Ala Tyr Leu Ser Val Asn
    290                 295                 300

Arg Glu Trp Tyr Ala Arg Ile Arg Ala Glu Val Asp Ala Ala Val Ala
305                 310                 315                 320

Lys His Arg Arg Ser Arg Val Glu Ser Ala Pro Glu Val Leu Leu Arg
                325                 330                 335

Leu Ser Met Gly Glu Trp Glu Ser Glu Phe Pro Met Ile Cys Thr Ala
            340                 345                 350

Leu Arg Glu Thr Ile Arg Met Ile Leu Gln Leu Thr Ser Ile Arg Lys
        355                 360                 365

Asn Ile Ser Gly Lys Asp Ile Gln Ile Ala Glu Thr Gly Ile Ile Ala
    370                 375                 380

Leu Ser Thr
385

<210> SEQ ID NO 4
<211> LENGTH: 377
<212> TYPE: PRT
<213> ORGANISM: Hirsutella minnesotensis

<400> SEQUENCE: 4

Ser Leu Ile Pro Gly Pro Glu Ala Trp Pro Ala Ser Val Leu Met Leu
1               5                   10                  15

Leu Leu Thr Gly Ala Ala Ala Ile Val Ile Gln Met Val Ala Ser Arg
            20                  25                  30

Pro Ser Phe Pro Ser Gly Ala Pro Arg Leu Leu Lys Gly Thr Pro Ile
        35                  40                  45

Leu Gly Cys Leu Asp Phe Phe Arg Ser Arg Ser Glu Phe Leu Leu Lys
    50                  55                  60

Gly Arg Asp Asn Asp Pro Ser Arg Gln Phe Ser Phe Tyr Tyr Gly Pro
```

```
            65                  70                  75                  80
        His Pro Ile Val Val Ser Gly Ser Ser Ala Arg Ser Phe Phe Tyr
                        85                  90                  95
        Asn Ala Arg Gly Leu Asp Leu Gln Ala Gly Phe Ser Thr Leu Phe Ala
                    100                 105                 110
        Ala Gly Pro Ser Leu Asp His Leu His Thr Gly Asp Ile Arg Thr Ile
                    115                 120                 125
        Phe Ile Thr Ser Phe Lys His Leu Met His Lys Asp Arg Leu Gln Ala
            130                 135                 140
        Asn Leu His His Leu Val Asn Asp Ala Asp Val Ala Leu Gly Gly Leu
        145                 150                 155                 160
        Asp Val Ser Arg Pro Val Glu Pro Phe Arg Val Met Leu His Leu Ile
                        165                 170                 175
        Tyr Gln Leu Thr His Arg Thr Leu Gly Ser Asn Asp Ile Ala Glu Asn
                    180                 185                 190
        Pro Lys Leu Leu Ala Lys Thr Leu Glu Ser Phe Gly Arg Leu Asp Asp
                    195                 200                 205
        Ser Ser Ala Met Glu Ile Met Phe Pro Trp Val Pro Trp Pro Ser Lys
            210                 215                 220
        Met Lys Lys Met Val Ala Gly Ala Lys Leu His Arg Thr Phe Ser Asn
        225                 230                 235                 240
        Ile Met Asn Asp Arg Arg Thr Gly Arg Val Glu Pro Asp Ala Met
                        245                 250                 255
        Gln Thr Leu Met Asp Gln Gly His Gln Asp Leu Ile Ile Ser Ile Phe
                    260                 265                 270
        Ile Ile Gly Ala Leu Phe Ala Gly Leu Ile Asn Ser Ala Phe Ser Ala
                    275                 280                 285
        Ala Trp Ile Leu Ala Tyr Leu Thr Asn Asn Pro Glu Trp Tyr Ala Arg
            290                 295                 300
        Ile Arg Asn Glu Ile Asp Ala Ala Val Ala Lys His Arg Tyr Ser Glu
        305                 310                 315                 320
        Gln Glu Ser Ala Pro Lys Val Leu Ala Arg Leu Ser Met Asp Asp Trp
                        325                 330                 335
        Glu Thr Glu Phe Pro Met Val Asp Leu Ala Leu Arg Glu Thr Ile Arg
                    340                 345                 350
        Val Ile Leu Gln Gly Ser Ser Met Arg Lys Asn Val Ser Gly Gln Asp
                    355                 360                 365
        Ile Pro Ile Gly Asp Thr Gly Gln Ile
            370                 375

<210> SEQ ID NO 5
<211> LENGTH: 1844
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 5
cgagcatcaa gccgcgtgcc gagggaatgt cggacattgg ccgaaggcgt acatggaccg      60
tatacatcaa gccgcaccac tgactgcagc ctagaaacag atgggcatag ttggatatgt     120
tgcttcgtta ttacgtaccg ccaatatcct cgatgtgccc ctggtgttgc tgctctgcag     180
actcgctacg gacctcggct ggaccgcacc catgctataa gccccatcaa ggccgatccg     240
gttctgcttc atatcctctt gcattaatcc cgaagcccga cctttcgtga ctgtgctctg     300
```

```
gcggaacaca gatttccggt ttgcctactc agcggcaaca gttggtaccc cgtgacgatc    360
cttggagctt gctgccggga taatcatggc atcaacccgg gttcttgcgc tcccaatgtt    420
ccccatcttg atgactattt ctctttacct cggatactac actcggcggc ccattcgcct    480
tgtctattgc ggcataatat tatgcgcctt tcttagtgtc gtgcgctgcg caccacagga    540
cgaggtaggg agtgattatg ccttcgggat gagtacatac atatccaagc ccctaccgtg    600
ctgaagagtg ttgacgcgtc gagtaaaata gtcggttgcg cgtgcctttg caaggcattc    660
cagatgctcg tcatcgagag agacatctac gccgactatt acgagttgga tgacaaggaa    720
aagacgcccg tcagatacag gagcctatcg agttggggga atgggagtg gtgccttgcg    780 cactgcttct ctgctcgagg gattggcttt agctgggcca tccctcacct tcccgaggcc    840
atgcccagca acacgacgat tcgggactac ctgcgggcga cgctcttaa tctcggctgg    900 ctctaccttg tccaggatct cggacgctcg ctgctatctg cggacttgtt tgctcacgag    960
ggcgtcggag ccagcgatac aaagggcggc gcccgttttc tgaccgtcta ttcacttgga   1020
atcggggcct tgttgaacat cgacatgcca taccgtgctg tatgcgccat gggcatggcc   1080
agcgggtgct tctggaccag gccgcaccac aaccggcctg cagtcggccg ctggcgggac   1140
gcatggacgc tgcgacgctt ctggggccgc gtctggcacc agacgttccg caaggtacgt   1200
acatatgcct gcagcggccg gccggtgagg agtgctaacg tctgtcccag ccctggcagt   1260
cgatcggtca atggattgcc tgggaagtca tgcgcgccct caaaggctcc cttgtctcga   1320
gatacgtcca ggtctacact tcttttctgc tatcggcctt gatgcacgtt gccgctgcgc   1380
ggatggccga tccgcaccga cgctcctgcg ccgggacttg gatcttcttt ctcatgcagg   1440
ccaacggcat cgtggccgag gatgttgtgc agtgggctgg taagaagacg gggatgcggg   1500
agtcgtccag cctgacccgt ttcctgggcc gggcttgggt gctttgctgg tttgcatgga   1560
cggcgccgtg gttctttggg gatatcgccg acgttggcct gatccgcctc gagacgttcc   1620
ctctgtcggt gactcggggt ctgtggaatc ggcagtggaa gatgtgagac ggtgtggaaa   1680
gtgatgatga tgtattcagc tatctaggct atccacacat gtggcacaac gagggcatag   1740
gtattatcgt gcgctaggca cgtgacttgg aaaagatatc ccctcgcagg atgataaagg   1800
tagaaaaaag gattgaatta aagctatctt ctattatata aata                    1844
```

<210> SEQ ID NO 6
<211> LENGTH: 948
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 6

```
atgctcgtca tcgagagaga catctacgcc gactattacg agttggatga caaggaaaag     60
acgcccgtca gatacaggag cctatcgagt tgggggaaat gggagtggtg ccttgcgcac    120
tgcttctctg ctcgagggat tggctttagc tgggccatcc ctcaccttcc cgaggccatg    180
cccagcaaca cgacgattcg ggactacctg cgggcgagcg ctcttaatct cggctggctc    240
taccttgtcc aggatctcgg acgctcgctg ctatctgcgg acttgtttgc tcacgagggc    300
gtcggagcca gcgatacaaa gggcggcgcc cgttttctga ccgtctattc acttggaatc    360
ggggccttgt tgaacatcga catgccatac cgtgctgtat gcgccatggg catggccagc    420
gggtgcttct ggaccaggcc gcaccacaac cggcctgcag tcggccgctg cgggacgca    480
```

-continued

```
tggacgctgc gacgcttctg gggccgcgtc tggcaccaga cgttccgcaa gccctggcag      540
tcgatcggtc aatggattgc ctgggaagtc atgcgcgccc tcaaaggctc ccttgtctcg      600
agatacgtcc aggtctacac ttctttctg ctatcggcct tgatgcacgt tgccgctgcg       660
cggatggccg atccgcaccg acgctcctgc gccgggactt ggatcttctt tctcatgcag     720
gccaacggca tcgtggccga ggatgttgtg cagtgggctg gtaagaagac ggggatgcgg     780
gagtcgtcca gcctgacccg tttcctgggc cgggcttggg tgctttgctg gtttgcatgg     840
acggcgccgt ggttctttgg ggatatcgcc gacgttggcc tgatccgcct cgagacgttc     900
cctctgtcgg tgactcgggg tctgtggaat cggcagtgga agatgtga                 948
```

<210> SEQ ID NO 7
<211> LENGTH: 315
<212> TYPE: PRT
<213> ORGANISM: Unknown
<220> FEATURE:
<223> OTHER INFORMATION: Epichloe sp. Lolium perenne taxonomic group 3 (LpTG-3)

<400> SEQUENCE: 7

```
Met Leu Val Ile Glu Arg Asp Ile Tyr Ala Asp Tyr Tyr Glu Leu Asp
1               5                   10                  15

Asp Lys Glu Lys Thr Pro Val Arg Tyr Arg Ser Leu Ser Ser Trp Gly
            20                  25                  30

Lys Trp Glu Trp Cys Leu Ala His Cys Phe Ser Ala Arg Gly Ile Gly
        35                  40                  45

Phe Ser Trp Ala Ile Pro His Leu Pro Glu Ala Met Pro Ser Asn Thr
    50                  55                  60

Thr Ile Arg Asp Tyr Leu Arg Ala Ser Ala Leu Asn Leu Gly Trp Leu
65                  70                  75                  80

Tyr Leu Val Gln Asp Leu Gly Arg Ser Leu Leu Ser Ala Asp Leu Phe
                85                  90                  95

Ala His Glu Gly Val Gly Ala Ser Asp Thr Lys Gly Gly Ala Arg Phe
            100                 105                 110

Leu Thr Val Tyr Ser Leu Gly Ile Gly Ala Leu Leu Asn Ile Asp Met
        115                 120                 125

Pro Tyr Arg Ala Val Cys Ala Met Gly Met Ala Ser Gly Cys Phe Trp
    130                 135                 140

Thr Arg Pro His His Asn Arg Pro Ala Val Gly Arg Trp Arg Asp Ala
145                 150                 155                 160

Trp Thr Leu Arg Arg Phe Trp Gly Arg Val Trp His Gln Thr Phe Arg
                165                 170                 175

Lys Pro Trp Gln Ser Ile Gly Gln Trp Ile Ala Trp Glu Val Met Arg
            180                 185                 190

Ala Leu Lys Gly Ser Leu Val Ser Arg Tyr Val Gln Val Tyr Thr Ser
        195                 200                 205

Phe Leu Leu Ser Ala Leu Met His Val Ala Ala Arg Met Ala Asp
    210                 215                 220

Pro His Arg Arg Ser Cys Ala Gly Thr Trp Ile Phe Phe Leu Met Gln
225                 230                 235                 240

Ala Asn Gly Ile Val Ala Glu Asp Val Val Gln Trp Ala Gly Lys Lys
                245                 250                 255

Thr Gly Met Arg Glu Ser Ser Leu Thr Arg Phe Leu Gly Arg Ala
            260                 265                 270
```

```
Trp Val Leu Cys Trp Phe Ala Trp Thr Ala Pro Trp Phe Gly Asp
            275                 280                 285

Ile Ala Asp Val Gly Leu Ile Arg Leu Glu Thr Phe Pro Leu Ser Val
        290                 295                 300

Thr Arg Gly Leu Trp Asn Arg Gln Trp Lys Met
305                 310                 315

<210> SEQ ID NO 8
<211> LENGTH: 391
<212> TYPE: PRT
<213> ORGANISM: Oidiodendron maius

<400> SEQUENCE: 8

Met Glu Arg Ala Asn Phe Thr Leu Leu Val Tyr Leu Leu Val Pro Val
1               5                   10                  15

Asn Leu Phe Ile Ala Ser Gln Thr Pro Lys Arg Phe Arg Phe Leu Tyr
            20                  25                  30

Ala Val Phe Gln Leu Gly Leu Tyr Phe Ala Ile Val Leu Leu Val Pro
        35                  40                  45

Pro Gly Ser Val Pro Ser Ser Asp Tyr Thr Phe Gly Thr Thr Phe Tyr
    50                  55                  60

Ser Val Leu Ala Ala Phe Asn Phe Phe Phe Cys Asp Pro Tyr Glu
65                  70                  75                  80

Glu His Trp Gln Ile Ala Pro Glu Glu Asp Lys Ile Asp Gln Gly Arg
                85                  90                  95

Asp Arg Ser Arg Gln Ser Ser Pro Val Lys Tyr Lys Asp Leu Asp Leu
            100                 105                 110

Arg Ala Ser Val Leu Trp Cys Ile Ser Asn Ala Phe Ala Leu Arg Gly
        115                 120                 125

Ile Gly Trp Asn Trp Arg Ile Pro His Leu Pro Pro Gly Pro Thr Arg
    130                 135                 140

Gly Ile Ser Arg Val Pro Tyr Leu Ile Asp Val Gly Thr Thr Leu Leu
145                 150                 155                 160

Lys Leu Tyr Leu Leu His Asp Phe Ser Ala Thr Leu Leu Glu Lys Val
                165                 170                 175

Thr Leu Gly Gly Gln Leu Pro Leu Glu Asn Ile Arg Leu Asp Leu Arg
            180                 185                 190

Thr Val Ala Val Val Ser Phe Ala Val Ser Ser Ile Thr Leu Ile Glu
        195                 200                 205

Phe Gly Tyr Gln Ile Ile Cys Phe Ala Gly Ala Thr Gly Leu Phe
    210                 215                 220

Trp Thr Arg Phe Gln Asp Asn His Pro Val Ile Gly Ser Val Tyr Glu
225                 230                 235                 240

Gly Tyr Thr Ile Gly Arg Phe Trp Gly Arg Val Trp His Gln Asn Met
                245                 250                 255

Arg Arg Ala Pro Gly Lys Tyr Leu Ala Gln Lys Val Leu His Val Lys
            260                 265                 270

Arg Gly Gly Leu Val Ser Arg Tyr Val Gln Ser Tyr Thr Ala Phe Phe
        275                 280                 285

Leu Ser Gly Val Tyr His Tyr Ile Gly Ala Lys Ser Ser Leu Pro His
    290                 295                 300

Glu Gln Leu Asn Arg Thr Cys Trp Phe Phe Leu Leu Gln Pro Asn Leu
305                 310                 315                 320

Met Leu Ile Glu Asp Phe Ala Leu Trp Phe Gly Lys Glu Lys Leu Gly
                325                 330                 335
```

```
Leu Lys Ser Pro Arg Trp Thr Cys Leu Gly Tyr Val Trp Thr Phe Val
        340                 345                 350

Met Leu Thr Val Thr Ala Ala Gly Phe Val Asp Asp Cys Ile Arg His
        355                 360                 365

Gln Leu Val Pro Pro Thr Ser Ala Phe Ser Phe Ser Leu Ala Ala Leu
        370                 375                 380

Leu Ile Gln Lys Trp Glu Leu
385                 390

<210> SEQ ID NO 9
<211> LENGTH: 1672
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 9
```

| | | | | | |
|---|---|---|---|---|---|
| ccgccaccga | cataacgagc | cgttgtctat | aagagtccaa | tcgtgccagg | acgcaacgtc | 60 |
| caagtagccc | tgattcttgc | tcaacccgac | gtggctcgct | ttactggctt | agagacctca | 120 |
| tctgacggcc | agtctctgat | tcgaaaccca | tttgcacgac | cgaccaagat | gggcacctgt | 180 |
| tccactcgcg | taggcgagac | gccatcgaaa | ccagcagatg | tgacgccgcc | tgagccatgg | 240 |
| caggccctag | ctcagggtct | agggttcgcc | aatgagaacg | agaggtactg | gtggtccaaa | 300 |
| cttgcccccc | tggctggcaa | gatgatgaag | tgggggcagt | actcgacgcc | ggagcagtac | 360 |
| agagtcctgg | cattcataca | gcgtatatt  | gtccctagct | gtggcccaag | gcctggggat | 420 |
| ggcggtgatc | tgttctggaa | ggtgtttctc | aactacgatt | gcacccctat | ccagctcagt | 480 |
| ctcaactacc | acgatgggaa | gatgacgctt | cggacagctc | atatacctat | cagcaatatc | 540 |
| tccggcacag | cagaagaccc | cattaaccag | aaggctgcga | tagatgccat | ggtccgccag | 600 |
| caacaggtcc | tgccgtccca | ggacatgcgc | tggtttaacc | actttgtatc | taagctcttc | 660 |
| ctggatcgag | atacggcggc | caccctcaag | gccaaggtgg | acgagttcca | gatccggcag | 720 |
| ggagttcagt | gcatgctcag | ccacgacttt | cccgacaatc | acatccagtg | taagctagcc | 780 |
| tttgcctccc | actggaagtc | tatcgccact | ggccttgata | ggaggaagt  | tatctgggat | 840 |
| gcaatcttgg | ggttagggga | cgacgttatt | ccgtataagc | cagtgctcgc | tatgctccag | 900 |
| caatactcaa | cgtccaaaag | tgccgcagct | gcaggggcac | atccgatctt | tttcgccatc | 960 |
| gactcggtgc | tcaaagacga | ctatacaagc | tcacgtatca | agatctattt | tgttacccac | 1020 |
| cgaactgcct | ttaacgtcat | ggttgacatc | tatacccta  | gtggtttgct | aatggggcct | 1080 |
| tgtattgaaa | agggcacgca | ggccttgagg | acactctgga | aggccgtgct | caatgttccc | 1140 |
| gaggggtggc | cagacgataa | ggatctaccc | atcaacccca | atggctgtgc | ggcagtcatc | 1200 |
| ttcaactttg | aggtccggcc | tggcgccgag | ttcccggctc | ctaagattta | cctcccagcc | 1260 |
| cattactatg | gccgacccga | cttggagatt | gctgatggaa | tggaccgctt | tttcctgagc | 1320 |
| cagggatggg | atggtatttta | ccctggctat | aagaaaaact | acctcaagtg | cttgtctgtt | 1380 |
| cttgttgccc | ctggccttct | ttccctttgc | ccttggctaa | cagtaaggta | gtatgaactc | 1440 |
| ggacaaccag | ctcacggctg | tgcaccacga | catttctttt | tcattcaagg | ggactaaccc | 1500 |
| ctatgttacc | gtctattata | agcctgagtt | gcatttggag | gctgagtagg | cggtggacca | 1560 |
| agcggtaagg | ttagatgggg | tgttgattcc | ttaattgctt | ccctttattt | ttgttatttt | 1620 |
| ttgttacgta | gcagagttaa | tggcatctgt | cctatgcagg | tatttccagg | gg | 1672 |

<210> SEQ ID NO 10
<211> LENGTH: 1263
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 10

| | | |
|---|---|---|
| atgggcacct gttccactcg cgtaggcgag acgccatcga aaccagcaga tgtgacgccg | 60 |
| cctgagccat ggcaggccct agctcagggt ctagggttcg ccaatgagaa cgagaggtac | 120 |
| tggtggtcca aacttgcccc cctggctggc aagatgatga agtggggggca gtactcgacg | 180 |
| ccggagcagt acagagtcct ggcattcata cacgcgtata ttgtccctag ctgtggccca | 240 |
| aggcctgggg atggcggtga tctgttctgg aaggtgtttc tcaactacga ttgcaccccct | 300 |
| atccagctca gtctcaacta ccacgatggg aagatgacgc ttcggacagc tcatatacct | 360 |
| atcagcaata tctccggcac agcagaagac cccattaacc agaaggctgc gatagatgcc | 420 |
| atggtccgcc agcaacaggt cctgccgtcc caggacatgc gctggtttaa ccactttgta | 480 |
| tctaagctct tcctggatcg agatacggcg gccacccctca aggccaaggt ggacgagttc | 540 |
| cagatccggc agggagttca gtgcatgctc agccacgact ttcccgacaa tcacatccag | 600 |
| tgtaagctag cctttgcctc ccactggaag tctatcgcca ctggccttga taggaggaa | 660 |
| gttatctggg atgcaatctt ggggttaggg gacgacgtta ttccgtataa gccagtgctc | 720 |
| gctatgctcc agcaatactc aacgtccaaa agtgccgcag ctgcaggggc acatccgatc | 780 |
| tttttcgcca tcgactcggt gctcaaagac gactatacaa gctcacgtat caagatctat | 840 |
| tttgttaccc accgaactgc ctttaacgtc atggttgaca tctatacccct aggtggtttg | 900 |
| ctaatggggc cttgtattga aaagggcacg caggccttga ggacactctg gaaggccgtg | 960 |
| ctcaatgttc ccgaggggtg gccagacgat aaggatctac ccatcaaccc caatggctgt | 1020 |
| gcggcagtca tcttcaactt tgaggtccgg cctggcgccg agttcccggc tcctaagatt | 1080 |
| tacctcccag cccattacta tggccgaccc gacttggaga ttgctgatgg aatggaccgc | 1140 |
| ttttttcctga gccagggatg ggatggtatt taccctggct ataagaaaaa ctacctcaag | 1200 |
| tgcttgtctg ttcttgttgc ccctggcctt cttttcccttt gcccttggct aacagtaagg | 1260 |
| tag | 1263 |

<210> SEQ ID NO 11
<211> LENGTH: 420
<212> TYPE: PRT
<213> ORGANISM: Unknown
<220> FEATURE:
<223> OTHER INFORMATION: Epichloe sp. Lolium perenne taxonomic group 3
      (LpTG-3)

<400> SEQUENCE: 11

Met Gly Thr Cys Ser Thr Arg Val Gly Glu Thr Pro Ser Lys Pro Ala
1               5                   10                  15

Asp Val Thr Pro Pro Glu Pro Trp Gln Ala Leu Ala Gln Gly Leu Gly
            20                  25                  30

Phe Ala Asn Glu Asn Glu Arg Tyr Trp Trp Ser Lys Leu Ala Pro Leu
        35                  40                  45

Ala Gly Lys Met Met Lys Trp Gly Gln Tyr Ser Thr Pro Glu Gln Tyr
    50                  55                  60

```
Arg Val Leu Ala Phe Ile His Ala Tyr Ile Val Pro Ser Cys Gly Pro
 65                  70                  75                  80

Arg Pro Gly Asp Gly Asp Leu Phe Trp Lys Val Phe Leu Asn Tyr
                 85                  90                  95

Asp Cys Thr Pro Ile Gln Leu Ser Leu Asn Tyr His Asp Gly Lys Met
                100                 105                 110

Thr Leu Arg Thr Ala His Ile Pro Ile Ser Asn Ile Ser Gly Thr Ala
            115                 120                 125

Glu Asp Pro Ile Asn Gln Lys Ala Ala Ile Asp Ala Met Val Arg Gln
            130                 135                 140

Gln Gln Val Leu Pro Ser Gln Asp Met Arg Trp Phe Asn His Phe Val
145                 150                 155                 160

Ser Lys Leu Phe Leu Asp Arg Asp Thr Ala Ala Thr Leu Lys Ala Lys
                165                 170                 175

Val Asp Glu Phe Gln Ile Arg Gln Gly Val Gln Cys Met Leu Ser His
                180                 185                 190

Asp Phe Pro Asp Asn His Ile Gln Cys Lys Leu Ala Phe Ala Ser His
                195                 200                 205

Trp Lys Ser Ile Ala Thr Gly Leu Asp Lys Glu Glu Val Ile Trp Asp
210                 215                 220

Ala Ile Leu Gly Leu Gly Asp Asp Val Ile Pro Tyr Lys Pro Val Leu
225                 230                 235                 240

Ala Met Leu Gln Gln Tyr Ser Thr Ser Lys Ser Ala Ala Ala Gly
                245                 250                 255

Ala His Pro Ile Phe Phe Ala Ile Asp Ser Val Leu Lys Asp Asp Tyr
                260                 265                 270

Thr Ser Ser Arg Ile Lys Ile Tyr Phe Val Thr His Arg Thr Ala Phe
                275                 280                 285

Asn Val Met Val Asp Ile Tyr Thr Leu Gly Gly Leu Leu Met Gly Pro
                290                 295                 300

Cys Ile Glu Lys Gly Thr Gln Ala Leu Arg Thr Leu Trp Lys Ala Val
305                 310                 315                 320

Leu Asn Val Pro Glu Gly Trp Pro Asp Asp Lys Asp Leu Pro Ile Asn
                325                 330                 335

Pro Asn Gly Cys Ala Ala Val Ile Phe Asn Phe Glu Val Arg Pro Gly
                340                 345                 350

Ala Glu Phe Pro Ala Pro Lys Ile Tyr Leu Pro Ala His Tyr Tyr Gly
                355                 360                 365

Arg Pro Asp Leu Glu Ile Ala Asp Gly Met Asp Arg Phe Phe Leu Ser
370                 375                 380

Gln Gly Trp Asp Gly Ile Tyr Pro Gly Tyr Lys Lys Asn Tyr Leu Lys
385                 390                 395                 400

Cys Leu Ser Val Leu Val Ala Pro Gly Leu Leu Ser Leu Cys Pro Trp
                405                 410                 415

Leu Thr Val Arg
            420

<210> SEQ ID NO 12
<211> LENGTH: 394
<212> TYPE: PRT
<213> ORGANISM: Ophiocordyceps unilateralis

<400> SEQUENCE: 12

Met Ala Ala Ser Pro Thr Tyr Glu Asn Gly Thr Pro Ser Gln Pro Trp
 1               5                  10                  15
```

Gln Ala Leu Ala Gln Gly Leu Gly Tyr Val Asn Gln Asp Glu Gln Tyr
            20                  25                  30

Trp Trp Ser Lys Val Gly Pro Leu Ala Gln Arg Leu Met Glu Trp Ala
        35                  40                  45

Arg Tyr Ser Thr Pro Glu Arg Tyr Arg Val Leu Ala Phe Ile Tyr Thr
50                  55                  60

Tyr Ile Val Pro Ala Cys Gly Pro Lys Pro Asp Asp Asn Gly Gln Val
65                  70                  75                  80

Phe Trp Lys Thr Tyr Ile Asn Tyr Asp Cys Thr Pro Ile Gln Leu Ser
                85                  90                  95

Leu Asn Phe His Asp Lys Lys Val Thr Phe Arg Thr Ala Asn Ile Ser
            100                 105                 110

Ser Ser Asp Ile Ser Gly Thr Ala Lys Asp Pro Ile Asn Gln Gln Ala
        115                 120                 125

Ala Val Asp Ala Met Ile Lys Gln Lys Arg Val Leu Pro Ser Gln Asn
130                 135                 140

Met Arg Trp Phe Asn His Phe Met Ser Lys Leu Phe Leu Glu Pro Glu
145                 150                 155                 160

Ala Ala Ala Ala Leu Lys Ala Lys Ala Asp Glu Phe Gln Ile Arg Asn
                165                 170                 175

Gly Val Gln Cys Met Leu Ser His Asp Phe Pro Asn Ser Gln Val Gln
            180                 185                 190

Cys Lys Ala Phe Phe Ala Pro Asn Trp Lys Ala Phe Ala Thr Gly Ile
        195                 200                 205

Glu Met Lys Asp Val Ile Trp Asp Ala Ile Met Ala Leu Gly Asp Asp
210                 215                 220

Ile Leu Pro Tyr Lys Ser Gly Leu Ala Ile Leu Asp Arg Phe Thr Thr
225                 230                 235                 240

Ser Ala Ser Ala Ala Ala Gly Ala Val Pro Val Cys Phe Ala Phe
                245                 250                 255

Asp Ser Val Leu Glu Gly Asp Tyr Lys Asn Ser Arg Ile Lys Ile Tyr
            260                 265                 270

Tyr Ala Thr Leu Arg Thr Ala Phe Asp Val Met Val Glu Ile Tyr Thr
        275                 280                 285

Leu Gly Gly Leu Leu Thr Gly Pro Glu Met Glu Lys Gly Val Gln Ala
290                 295                 300

Leu Arg Met Leu Trp Asn Ala Val Asn Ile Pro Asp Gly Trp Pro
305                 310                 315                 320

Asp Asp Thr Asp Leu Pro Ala Asn Pro His Arg Phe Ala Ala Val Leu
                325                 330                 335

Phe Asn Phe Glu Ile Arg His Gly Ala Glu Leu Pro Val Pro Gln Ile
            340                 345                 350

Tyr Ile Pro Ala His Tyr Gly Arg Ser Asp Leu Glu Ile Ala Asp
        355                 360                 365

Gly Val Asp Arg Phe Phe Gln Ser Gln Gly Leu Asp Ala Asp Tyr Pro
370                 375                 380

Pro Tyr Lys Glu Asn Tyr Ile Lys Cys Leu
385                 390

<210> SEQ ID NO 13
<211> LENGTH: 1992
<212> TYPE: DNA
<213> ORGANISM: Unknown
<220> FEATURE:

<223> OTHER INFORMATION: Epichloe sp. Lolium perenne taxonomic group 3 (LpTG-3)

<400> SEQUENCE: 13

```
tcctgaccat gttggctccg ccaacggtga gactcaccct tgttctgaca cgcataccgc      60
gagagtaata tttcatgtac atgaacaaag cgcacggtgc ggtatcttgc gtttaattat     120
tgctccatat tgcaggctgc atatgcatta cgggagatgg ttgcattcaa tgccatatga     180
tgccgaggag agcggccgat acgcgccccg cctgtgctgt cccggattga agaaatgccc     240
gaggaaatgg gatctgttgg ctataatagc aagggaagta agcgtgtatc atccccggaa     300
ccatcaagca ctaccgcttt gaatcgcttc tcttcttgac agcatgggag accctcttcc     360
cggcaacacg cgagactgtc tctcccgcaa catgcgagac tcctcaaccg agaagctccc     420
cattctgtgg cggaccgact cccccctcaa ccagtacgat gaagcacggt gcagagtctt     480
caacggcagg cggcccgagc atttcccacg cgcaatcgtc caggccacga cgctcgacca     540
catcgtagcg gctgtgaggc tggccgtgga gtccgccgcc cctgtggccg tccgctcagg     600
tggccacagt ctctcctgct ggaccatgcg ccatgatgcc atcctcattg atctcaagga     660
ctttagctat ctaagctacg atgaagaaac acaccaagtc caggcctctc ccagtaccct     720
aacgggagaa ttgctcgagt ttcttgccca gaagcagcga ttctttcccg taggccactc     780
agggggcatt ggcctaggtg gctacctcct ccaagctgga atcggactca actgccgggt     840
atgcgtgctt gctctgcctg ccccatgctt gcctatccgt ttctcttcat ccactgacgg     900
caacgtctag ggctatgggt acgcatgcga gtctgtctct ggaatcgaca ttgttaccgc     960
cgatggctgc attaagcact gtgacaaaga agaaaacgct gatttgtatt gggccgctcg    1020
cggagctggg ccgggtgagt ccctctctga aagccttccg cattaaagcc gtggcaaatc    1080
taactaaaca gagttccctg ccattgtcac acgcttctac ctcgagactc gaccgatgcc    1140
ggtttgcaac cggagcacgt acatctggcc ggcgaccatg tatgaccagg ttttcccttg    1200
gctcgaccgc gtgagtagct cgtgtccatg tccccagcca agctcacgag gtttcaagct    1260
cttaactacg ctggacgaga acgtcgaggt tggcgtgttc ggatttacag tcccccaact    1320
caaccagccg gggctacacg tgctcgcaac agcattcgga gactcggatg aggatacccg    1380
gcgaatgctc acaccttca tcgacaccca cccccagga gcgattcacg cccaggactt     1440
tgtggcgact gacttcgcta gcgactacgt tctagataag acagtcctgc cgcaaggtgc    1500
tcgttacttc accgatagcg tctttctcaa gcctggcacc gacctagtgg tggcttgtaa    1560
ggacatgttt acaggactaa agcatccgcg gcattggca tattggcagc cgatgaagac    1620
cgccactgcc cgcaccttc ccgacatggc catgagcata catagcgacc attacgtatc    1680
cctactagga atctacgacg attccgccca agacgatgag cagacgtcct ggatcgtgga    1740
ttatatgcgt aagctggagc catttgtctt gggcacgttt gtggggatg cgcatgtgtt    1800
ggaaagaccg tctaattact ggtcagagga ggccaaagag cgagtgctcc gtgttggaaa    1860
gaagtgggat cctagtggaa gaattcgggg gatgctcctc agtgactcgt aggcagcgat    1920
ttatttaaag ggcgtgctta tcaggcaaac gcgtacgcgt aattagcacc cctaaaggta    1980
gctaaggtag ct                                                        1992
```

<210> SEQ ID NO 14
<211> LENGTH: 1440
<212> TYPE: DNA
<213> ORGANISM: Unknown
<220> FEATURE:

<223> OTHER INFORMATION: Epichloe sp. Lolium perenne taxonomic group 3
(LpTG-3)

<400> SEQUENCE: 14

```
atgggagacc ctcttcccgg caacacgcga gactgtctct cccgcaacat gcgagactcc      60
tcaaccgaga agctccccat tctgtggcgg accgactccc ccctcaacca gtacgatgaa     120
gcacggtgca gagtcttcaa cggcaggcgg cccgagcatt tcccacgcgc aatcgtccag     180
gccacgacgc tcgaccacat cgtagcggct gtgaggctgg ccgtggagtc cgccgcccct     240
gtggccgtcc gctcaggtgg ccacagtctc tcctgctgga ccatgcgcca tgatgccatc     300
ctcattgatc tcaaggactt tagctatcta agctacgatg aagaaacaca ccaagtccag     360
gcctctccca gtaccctaac gggagaattg ctcgagtttc ttgcccagaa gcagcgattc     420
tttcccgtag gccactcagg gggcattggc ctaggtggct acctcctcca agctggaatc     480
ggactcaact gccggggcta tgggtacgca tgcgagtctg tctctggaat cgacattgtt     540
accgccgatg gctgcattaa gcactgtgac aaagaagaaa acgctgattt gtattgggcc     600
gctcgcggag ctgggccgga gttccctgcc attgtcacac gcttctacct cgagactcga     660
ccgatgccgt tttgcaaccg gagcacgtac atctggccgg cgaccatgta tgaccaggtt     720
ttcccttggc tcgaccgcgt gagtagctcg tgtccatgtc cccagccaag ctcacgaggt     780
ttcaagctct taactacgct ggacgagaac gtcgaggttg gcgtgttcgg atttacagtc     840
ccccaactca accagccggg gctacacgtg ctcgcaacag cattcggaga ctcggatgag     900
gataccggc gaatgctcac acccttcatc gacacccacc cccaggagc gattcacgcc      960
caggactttg tggcgactga cttcgctagc gactacgttc tagataagac agtcctgccg    1020
caaggtgctc gttacttcac cgatagcgtc tttctcaagc ctggcaccga cctagtggtg    1080
gcttgtaagg acatgtttac aggactaaag catccgcgcg cattggcata ttggcagccg    1140
atgaagaccg ccactgcccg caccttccc gacatggcca tgagcataca tagcgaccat    1200
tacgtatccc tactaggaat ctacgacgat tccgcccaag acgatgagca gacgtcctgg    1260
atcgtggatt atatgcgtaa gctggagcca tttgtcttgg gcacgtttgt ggggatgcg    1320
catgtgttgg aaagaccgtc taattactgg tcagaggagg ccaaagagcg agtgctccgt    1380
gttggaaaga agtgggatcc tagtggaaga attcggggga tgctcctcag tgactcgtag    1440
```

<210> SEQ ID NO 15
<211> LENGTH: 479
<212> TYPE: PRT
<213> ORGANISM: Unknown
<220> FEATURE:
<223> OTHER INFORMATION: Epichloe sp. Lolium perenne taxonomic group 3
(LpTG-3)

<400> SEQUENCE: 15

```
Met Gly Asp Pro Leu Pro Gly Asn Thr Arg Asp Cys Leu Ser Arg Asn
1               5                   10                  15

Met Arg Asp Ser Ser Thr Glu Lys Leu Pro Ile Leu Trp Arg Thr Asp
            20                  25                  30

Ser Pro Leu Asn Gln Tyr Asp Glu Ala Arg Cys Arg Val Phe Asn Gly
        35                  40                  45

Arg Arg Pro Glu His Phe Pro Arg Ala Ile Val Gln Ala Thr Thr Leu
    50                  55                  60

Asp His Ile Val Ala Ala Val Arg Leu Ala Val Glu Ser Ala Ala Pro
65                  70                  75                  80
```

Val Ala Val Arg Ser Gly Gly His Ser Leu Ser Cys Trp Thr Met Arg
             85                  90                  95

His Asp Ala Ile Leu Ile Asp Leu Lys Asp Phe Ser Tyr Leu Ser Tyr
            100                 105                 110

Asp Glu Glu Thr His Gln Val Gln Ala Ser Pro Ser Thr Leu Thr Gly
            115                 120                 125

Glu Leu Leu Glu Phe Leu Ala Gln Lys Gln Arg Phe Phe Pro Val Gly
130                 135                 140

His Ser Gly Gly Ile Gly Leu Gly Gly Tyr Leu Leu Gln Ala Gly Ile
145                 150                 155                 160

Gly Leu Asn Cys Arg Gly Tyr Gly Tyr Ala Cys Glu Ser Val Ser Gly
            165                 170                 175

Ile Asp Ile Val Thr Ala Asp Gly Cys Ile Lys His Cys Asp Lys Glu
            180                 185                 190

Glu Asn Ala Asp Leu Tyr Trp Ala Ala Arg Gly Ala Gly Pro Glu Phe
            195                 200                 205

Pro Ala Ile Val Thr Arg Phe Tyr Leu Glu Thr Arg Pro Met Pro Val
210                 215                 220

Cys Asn Arg Ser Thr Tyr Ile Trp Pro Ala Thr Met Tyr Asp Gln Val
225                 230                 235                 240

Phe Pro Trp Leu Asp Arg Val Ser Ser Cys Pro Cys Pro Gln Pro
            245                 250                 255

Ser Ser Arg Gly Phe Lys Leu Leu Thr Thr Leu Asp Glu Asn Val Glu
            260                 265                 270

Val Gly Val Phe Gly Phe Thr Val Pro Gln Leu Asn Gln Pro Gly Leu
            275                 280                 285

His Val Leu Ala Thr Ala Phe Gly Asp Ser Asp Glu Asp Thr Arg Arg
290                 295                 300

Met Leu Thr Pro Phe Ile Asp Thr His Pro Pro Gly Ala Ile His Ala
305                 310                 315                 320

Gln Asp Phe Val Ala Thr Asp Phe Ala Ser Asp Tyr Val Leu Asp Lys
            325                 330                 335

Thr Val Leu Pro Gln Gly Ala Arg Tyr Phe Thr Asp Ser Val Phe Leu
            340                 345                 350

Lys Pro Gly Thr Asp Leu Val Val Ala Cys Lys Asp Met Phe Thr Gly
            355                 360                 365

Leu Lys His Pro Arg Ala Leu Ala Tyr Trp Gln Pro Met Lys Thr Ala
370                 375                 380

Thr Ala Arg Thr Leu Pro Asp Met Ala Met Ser Ile His Ser Asp His
385                 390                 395                 400

Tyr Val Ser Leu Leu Gly Ile Tyr Asp Asp Ser Ala Gln Asp Glu
            405                 410                 415

Gln Thr Ser Trp Ile Val Asp Tyr Met Arg Lys Leu Glu Pro Phe Val
            420                 425                 430

Leu Gly Thr Phe Val Gly Asp Ala His Val Leu Glu Arg Pro Ser Asn
            435                 440                 445

Tyr Trp Ser Glu Glu Ala Lys Glu Arg Val Leu Arg Val Gly Lys Lys
450                 455                 460

Trp Asp Pro Ser Gly Arg Ile Arg Gly Met Leu Leu Ser Asp Ser
465                 470                 475

<210> SEQ ID NO 16
<211> LENGTH: 444
<212> TYPE: PRT

<213> ORGANISM: Escovopsis weberi

<400> SEQUENCE: 16

Met Ala Asp Leu Pro Ile Ile Trp Arg Ser Asp Thr Glu Ser Ala Ala
1               5                   10                  15

Lys Tyr Glu Glu Ala Arg Cys Arg Ile Phe Asn Ile Arg Arg Pro Glu
            20                  25                  30

His Phe Pro Arg Ala Ile Val Lys Ala Thr Thr Leu Glu His Ile Val
        35                  40                  45

Ala Ala Val Lys Leu Ala Ala Glu Gln Gly Val Arg Val Val Ala Arg
    50                  55                  60

Ser Gly Gly His Gly Leu Ser Ala Trp Thr Leu Arg His Asn Ala Ile
65                  70                  75                  80

Leu Ile Asp Leu Gln Asn Phe Lys His Met Ser Tyr Asp Glu Lys
                85                  90                  95

Asn Glu Ala Gln Val Ser Pro Ser Thr Leu Ala Glu Glu Leu Leu Asp
            100                 105                 110

Phe Leu Ala Glu Arg Lys Arg Phe Phe Pro Ala Gly His Thr Gly Asp
        115                 120                 125

Ile Gly Leu Gly Gly Tyr Leu Leu Gln Gly Gly Ile Gly Leu Ser Cys
    130                 135                 140

Arg Gly Tyr Gly Tyr Ala Cys Glu Tyr Val Thr Gly Val Asp Val Val
145                 150                 155                 160

Thr Ala Glu Gly Asp Val Val His Ala Asp Glu Asn Glu Asn Ala Asp
                165                 170                 175

Leu Tyr Trp Ala Ala Arg Gly Ala Gly Pro Glu Phe Pro Ala Ile Val
        180                 185                 190

Thr Arg Phe Tyr Leu Lys Thr Ile Pro Leu Gln Pro Val Ala Lys Gly
    195                 200                 205

Cys Arg Tyr Ile Trp Pro Ala Val Met Tyr Asp Ala Ile Phe Ser Trp
210                 215                 220

Ile Asp Lys Ile Ser Ala Ser Leu Asp Glu His Val Asp Pro Ser Val
225                 230                 235                 240

Phe Gly Phe Met Ile Pro Gly Ile Asn Gln Pro Gly Leu Met Phe Ser
                245                 250                 255

Ala Ser Val Phe Ala Gln Thr Glu Glu Glu Ala Arg Arg Lys Leu Ala
        260                 265                 270

Pro Leu Val Glu Thr His Pro Pro Gly Ala Met Val Ala Glu Asp Phe
    275                 280                 285

Val Asp Ser Ser Ile Thr Thr Val Tyr Ala Gly Ser Arg Gln Phe Asn
290                 295                 300

Pro Pro Gly Cys Arg Tyr Phe Thr Asp Ser Val Phe Leu Lys Pro Gly
305                 310                 315                 320

Thr Asp Val Val Glu Ala Cys Arg His Met Phe Thr Gln Ile Pro Phe
                325                 330                 335

Pro Arg Gly Leu Ala Tyr Trp Gln Pro Leu Arg Ile Ser Pro Ala Arg
        340                 345                 350

Lys Gln Pro Asp Met Ala Leu Ser Ile Gln Ser Glu His Tyr Val Ser
    355                 360                 365

Leu Leu Ala Val Tyr Asp Asn Glu Ala Glu Asp Glu Ala Gln Thr Glu
370                 375                 380

Trp Val Ile Glu Gly Ile Arg Lys Leu Glu Pro Gln Ile His Gly Thr
385                 390                 395                 400

Phe Ile Ala Asp Ala His Pro Glu Met Arg Thr Ser Asn Tyr Trp Ser
                405                 410                 415

Glu Glu Ala Thr Ala Arg Leu Ala Ala Val Gly Ser Lys Trp Asp Pro
        420                 425                 430

Lys Gly Arg Ile Thr Gly Ile Val Val Arg Gln Glu
        435                 440

<210> SEQ ID NO 17
<211> LENGTH: 1263
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 17

```
ctaccttact gttagccaag ggcaaaggga agaaggcca ggggcaacaa gaacagacaa      60
gcacttgagg tagtttttct tatagccagg gtaaatacca tcccatccct ggctcaggaa    120
aaagcggtcc attccatcag caatctccaa gtcgggtcgg ccatagtaat gggctggag    180
gtaaatctta ggagccggga actcggcgcc aggccggacc tcaaagttga agatgactgc    240
cgcacagcca ttggggttga tgggtagatc cttatcgtct ggccacccct cgggaacatt    300
gagcacggcc ttccagagtg tcctcaaggc ctgcgtgccc ttttcaatac aaggccccat    360
tagcaaacca cctagggtat agatgtcaac catgacgtta aaggcagttc ggtgggtaac    420
aaaatagatc ttgatacgtg agcttgtata gtcgtctttg agcaccgagt cgatggcgaa    480
aaagatcgga tgtgccctg cagctgcggc acttttggac gttgagtatt gctgagcat     540
agcgagcact ggcttatacg gaataacgtc gtccctaac cccaagattg catcccagat    600
aacttcctcc ttatcaaggc cagtggcgat agacttccag tgggaggcaa aggctagctt    660
acactggatg tgattgtcgg gaaagtcgtg gctgagcatg cactgaactc cctgccggat    720
ctggaactcg tccaccttgg ccttgagggt gccgccgta tctcgatcca ggaagagctt    780
agatacaaag tggttaaacc agcgcatgtc ctgggacggc aggacctgtt gctggcggac    840
catggcatct atcgcagcct tctggttaat ggggtcttct gctgtgccgg agatattgct    900
gataggtata tgagctgtcc gaagcgtcat cttcccatcg tggtagttga gactgagctg    960
gatagggtg caatcgtagt tgagaaacac cttccagaac agatcaccgc catcccagg    1020
ccttgggcca cagctaggga caatatacgc gtgtatgaat gccaggactc tgtactgctc   1080
cggcgtcgag tactgccccc acttcatcat cttgccagcc aggggggcaa gtttggacca   1140
ccagtacctc tcgttctcat tggcgaaccc tagaccctga gctagggcct gccatggctc   1200
aggcggcgtc acatctgctg gtttcgatgg cgtctcgcct acgcgagtgg aacaggtgcc   1260
cat                                                                 1263
```

<210> SEQ ID NO 18
<211> LENGTH: 129
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 18

```
gcggtccatt ccatcagcaa tctccaagtc gggtcggcca tagtaatggg ctggaggta     60
aatcttagga gccgggaact cggcgccagg ccggacctca aagttgaaga tgactgccgc   120
``` acagccatt 129

<210> SEQ ID NO 19
<211> LENGTH: 95
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 19
cccaagattg catcccagat aacttcctcc ttatcaaggc cagtggcgat agacttccag    60
tgggaggcaa aggctagctt acactggatg tgatt    95

<210> SEQ ID NO 20
<211> LENGTH: 561
<212> TYPE: DNA
<213> ORGANISM: Unknown
<220> FEATURE:
<223> OTHER INFORMATION: Epichloe sp. Lolium perenne taxonomic group 3
      (LpTG-3)

<400> SEQUENCE: 20
gcggtccatt ccatcagcaa tctccaagtc gggtcggcca tagtaatggg ctgggaggta    60
aatcttagga gccgggaact cggcgccagg ccggacctca agttgaaga tgactgccgc   120 acagccattc caagattgca tcccagataa cttcctcctt atcaaggcca gtggcgatag   180
acttccagtg ggaggcaaag gctagcttac actggatgtg attgtcggga agtcgtggc   240 tgagcatgca ctgaactccc tgccggatct ggaactcgtc caccttggcc ttgagggtgg   300
ccgccgtatc tcgatccagg aagagcttag atacaaagtg gttaaaccag cgcatgtcct   360
gggacggcag gacctgttgc tggcggacca tggcatctat cgcagccttc tggttaatgg   420
ggtcttctgc tgtgccggag atattgctga taggtatatg agctgtccga agcgtcatct   480
tcccatcgtg gtagttgaga ctgagctgga taggggtgca atcgtagttg agaaacacct   540
tccagaacag atcaccgcca t    561

<210> SEQ ID NO 21
<211> LENGTH: 20
<212> TYPE: DNA
<213> ORGANISM: Artificial Sequence
<220> FEATURE:
<223> OTHER INFORMATION: Primer

<400> SEQUENCE: 21
tgtcgtccat cacagtttgc    20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gcgccgatgg tttctacaaa    20

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
gcctttcttc ttgcctgtca                                                                  20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
gaccgcctgt gtgttttgaa                                                                  20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
cacacagccc aagattgcat                                                                  20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tggaagtcta tcgccactgg                                                                  20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ggagttcagt gcatgctcag                                                                  20

<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ggcaagaaga aaggctcacc                                                                  20